US011350900B2

United States Patent
Smith

(10) Patent No.: US 11,350,900 B2
(45) Date of Patent: Jun. 7, 2022

(54) COMPUTER-ASSISTED TUMOR RESPONSE ASSESSMENT AND EVALUATION OF THE VASCULAR TUMOR BURDEN

(71) Applicant: AI METRICS, LLC, Hoover, AL (US)

(72) Inventor: Andrew Dennis Smith, Hoover, AL (US)

(73) Assignee: AI Metrics, LLC, Hoover, AL (US)

( * ) Notice: Subject to any disclaimer, the term of this patent is extended or adjusted under 35 U.S.C. 154(b) by 0 days.

(21) Appl. No.: 16/924,654

(22) Filed: Jul. 9, 2020

(65) Prior Publication Data

US 2020/0337665 A1   Oct. 29, 2020

Related U.S. Application Data

(63) Continuation of application No. 16/525,351, filed on Jul. 29, 2019, now Pat. No. 10,743,829, which is a (Continued)

(51) Int. Cl.
*G06K 9/00* (2022.01)
*A61B 6/00* (2006.01)
(Continued)

(52) U.S. Cl.
CPC .......... *A61B 6/5211* (2013.01); *G06T 7/0016* (2013.01); *G06T 7/90* (2017.01);
(Continued)

(58) Field of Classification Search
CPC ....... A61B 6/5211; G06T 7/90; G06T 7/0016; G06T 2207/10072; G06T 2207/20072;
(Continued)

(56) References Cited

U.S. PATENT DOCUMENTS 6,009,342 A   12/1999 Brasch et al.
9,826,951 B2  11/2017 Smith
(Continued)

OTHER PUBLICATIONS

Bornemann et al., "OncoTREAT: a software assistant for cancer therapy monitoring", International Journal of Computer Assisted Radiology, 2007, vol. 1, pp. 231-242.
(Continued)

*Primary Examiner* — Atiba O Fitzpatrick
(74) *Attorney, Agent, or Firm* — Workman Nydegger

(57) ABSTRACT

A computer-implemented method for determining and evaluating an objective tumor response to an anti-cancer therapy using cross-sectional images can include receiving cross-sectional images of digital medical image data and identifying target lesions within the cross-sectional images. For each of the target lesions, a target lesion type and anatomical location is identified, a segmenting tool is activated for segmenting the target lesions into regions of interest, lesion metrics are automatically extracted from the regions of interest according to tumor response criteria, and conformity of target lesion identification is monitored using rules associated with the tumor response criteria, prompting a user to address any nonconforming target lesion. The method also includes receiving a presence/absence of metastases, determining changes in lesions metrics, and deriving an objective tumor response based on the tumor response criteria.

18 Claims, 11 Drawing Sheets

Related U.S. Application Data continuation of application No. 15/797,391, filed on Oct. 30, 2017, now Pat. No. 10,413,266, which is a continuation of application No. 15/407,662, filed on Jan. 17, 2017, now Pat. No. 9,826,951, which is a continuation of application No. PCT/US2016/030823, filed on May 4, 2016.

(60) Provisional application No. 62/156,836, filed on May 4, 2015.

(51) Int. Cl.
 *G06T 7/00* (2017.01)
 *G06T 7/90* (2017.01)

(52) U.S. Cl.
 CPC ............ *G06T 2207/10072* (2013.01); *G06T 2207/20072* (2013.01); *G06T 2207/30096* (2013.01); *G06T 2207/30101* (2013.01); *G06V 2201/032* (2022.01)

(58) Field of Classification Search
 CPC ........... G06T 2207/30096; G06T 2207/30101; G06K 2209/053
 See application file for complete search history.

(56) References Cited

U.S. PATENT DOCUMENTS

| | | | |
|---|---|---|---|
| 9,931,093 B2 | 4/2018 | Smith | |
| 10,413,266 B2 | 9/2019 | Smith | |
| 2003/0016850 A1* | 1/2003 | Kaufman | G16H 40/63 382/128 |
| 2003/0199762 A1 | 10/2003 | Fritz et al. | |
| 2004/0029213 A1 | 2/2004 | Callahan et al. | |
| 2004/0267102 A1* | 12/2004 | Skladnev | A61B 5/442 600/315 |
| 2005/0043614 A1 | 2/2005 | Huizenga et al. | |
| 2006/0242146 A1 | 10/2006 | Piacsek et al. | |
| 2007/0100226 A1 | 5/2007 | Yankelevitz et al. | |
| 2009/0097727 A1 | 4/2009 | Jolly et al. | |
| 2009/0279754 A1 | 11/2009 | Gindele et al. | |
| 2010/0254589 A1 | 10/2010 | Gallagher | |
| 2011/0054236 A1 | 3/2011 | Yang et al. | |
| 2011/0243402 A1* | 10/2011 | Kadir | G06T 7/62 382/128 |
| 2012/0070055 A1 | 3/2012 | Liu et al. | |
| 2013/0129177 A1* | 5/2013 | Meinel | G06T 7/162 382/131 |
| 2014/0016845 A1 | 1/2014 | Gazit et al. | |
| 2014/0029815 A1* | 1/2014 | Kadir | G06T 7/50 382/128 |
| 2014/0314286 A1 | 10/2014 | Madabhushi et al. | |
| 2015/0078641 A1* | 3/2015 | Tan | G06T 7/12 382/131 |
| 2015/0110374 A1 | 4/2015 | Traughber et al. | |
| 2015/0356730 A1 | 12/2015 | Grove et al. | |
| 2016/0000368 A1 | 1/2016 | Wang et al. | |
| 2016/0122707 A1* | 5/2016 | Swee | C12N 9/52 424/93.7 |
| 2016/0157805 A1 | 6/2016 | Bathina et al. | |
| 2017/0231592 A1* | 8/2017 | Sevenster | A61B 6/461 600/407 |

OTHER PUBLICATIONS

Final Office Action received for U.S. Appl. No. 15/797,391, dated Aug. 30, 2018.
International Search Report and Written Opinion issued in PCT Application No. PCT/US2016/030823 dated Sep. 9, 2016.
Notice of Allowance issued in U.S. Appl. No. 16/525,351 dated May 6, 2020.
Notice of Allowance received for U.S. Appl. No. 15/797,391, dated May 15, 2019.
Notice of Allowance received for U.S. Appl. No. 15/797,391, dated Nov. 21, 2018.
Office Action issued in U.S. Appl. No. 16/525,351 dated Mar. 18, 2020.
Office Action issued in U.S. Appl. No. 16/525,351 dated Sep. 17, 2019.
Office Action received for U.S. Appl. No. 15/797,391, dated Feb. 8, 2018.
Office Action received for U.S. Appl. No. 15/797,391, dated Feb. 14, 2019.
P Therasse, New guidelines to evaluate the response to treatment in solid tumors, Journal of the National Cancer Institute, vol. 92, No. 3, pp. 205-216, 2000.
Rubin et al., "Automated Tracking of Quantitative Assessments of Tumor Burden in Clinical Trials", Translational Oncology, 2014, vol. 7, No. 1, pp. 23-35.
U.S. Appl. No. 15/797,360, filed Oct. 30, 2017, Notice of Allowance dated Feb. 14, 2018.

* cited by examiner

COMPUTER-ASSISTED TUMOR RESPONSE ASSESSMENT AND EVALUATION OF THE VASCULAR TUMOR BURDEN

CROSS-REFERENCE TO RELATED APPLICATIONS

This application is a continuation of U.S. patent application Ser. No. 16/525,351, filed Jul. 29, 2019, which is a continuation of U.S. patent application Ser. No. 15/797,391, filed Oct. 30, 2017, which is a continuation of U.S. patent application Ser. No. 15/407,662, filed Jan. 17, 2017, which is a continuation of International Application No. PCT/US2016/030823, filed May 4, 2016, which claims the benefit of U.S. Provisional Patent Application No. 62/156,836, filed May 4, 2015, the disclosures of which are incorporated herein by reference in their entirety.

BACKGROUND

Technical Field

The present invention relates generally to the collection, evaluation, and transformation of digital image files.

Background and Relevant Art

Advances in computing technology have resulted in a concomitant advance in medical device technologies, including within the field of diagnostic medicine. Particularly, the past century has demonstrated significant advances in medical imaging devices. Such advances have been hallmarked by the advent of radiologic devices such as computed tomography (CT; also known as x-ray computed tomography (x-ray CT) and computerized axial tomography scan (CT scan)), magnetic resonance imaging, and other radiologic devices that allow for the non-invasive viewing and exploration of internal structures of the body. These medical imaging devices allow physicians and clinicians to better document, treat, and understand pathologies, including cancer.

A variety of tumor response criteria have been developed to predict and/or evaluate the effects of anti-cancer therapies. However, there are issues with the known tumor response criteria being inconsistent, difficult to implement, narrowly tailored, expensive, and not reliably reproducible across multiple different institutions and readers. Further, the effects of some newer anti-cancer treatment therapies are difficult to determine with the current tumor response criteria.

Accordingly, there are a number of disadvantages in the art of data collection and management that can be addressed.

SUMMARY OF INVENTION

Technical Problem

There is a need for a method or tumor imaging biomarker for assessing tumor response to anti-cancer therapies that could provide a straightforward quantitative metric or set of quantitative metrics that is directly related to the main effect of newer anti-cancer therapies. This need is particularly exacerbated when considering the dearth of methods or tumor imaging biomarkers available for accurately assessing tumor response to anti-cancer therapies that cause tumor devascularization, including anti-angiogenic therapies. Current tumor imaging biomarkers and tumor response criteria fail to directly quantify changes in the vascular tumor burden on cross-sectional images to effectively monitor response to anti-cancer therapies, including anti-angiogenic therapy, and to predict long-term response to anti-angiogenic therapy.

Further, the implementation of available tumor response criteria suffers from user-induced error, whether by miscalculations of tumor metrics, measurement errors, data transfer errors, mathematical errors, or by selecting target lesions that do not meet the standards of a given tumor response criteria. Additionally, there is a considerable amount of intra- and inter-observer variability in determining an objective tumor response with conventional methods. Each of the foregoing may cause an incorrect classification of tumor response, which could negatively impact patient care, quality of life, and survival.

Solution to Problem

Implementations of the present invention comprise computer-implemented methods and systems and computer programmable products configured to determine and evaluate an objective tumor response to an anti-cancer therapy using cross-sectional images. In some embodiments, this can include receiving cross-sectional images of digital medical image data and identifying target lesions within the cross-sectional images. For each of the target lesions, a target lesion type and anatomical location is identified, a segmenting tool is activated for segmenting the target lesions into regions of interest, lesion metrics are automatically extracted from the regions of interest according to tumor response criteria, and conformity of target lesion identification is monitored using rules associated with the tumor response criteria, prompting a user to address any nonconforming target lesion. The method also includes receiving a presence/absence of metastases, determining changes in lesions metrics, and deriving an objective tumor response based on the tumor response criteria.

Embodiments of the foregoing may be implemented in a computer assisted manner for assessing and post-processing digital radiologic cross-sectional images of tumors to derive one or more tumor metrics, including total tumor burden and vascular tumor burden and may further derive objective tumor response via one or more tumor response criteria. In some embodiments, a user interacts with a computer interface responsive to user selections and which updates a plurality of tumor metrics in response to user input and which may synthesize and display a report to the user summarizing results, including a vascular tumor burden and an objective tumor response.

Embodiments of the present disclosure provide a technical solution to the aforementioned technical problems associated with reliably and directly quantifying changes in the vascular tumor burden using cross-sectional images, with effectively monitoring responses to anti-cancer therapies whose main effect is to cause devascularization of tumors, including anti-angiogenic therapy, and with predicting long-term response to anti-angiogenic therapy. Further, embodiments of the present disclosure provide a technical solution to the aforementioned technical problem of incorrectly classifying tumor response based on user error and may also act to reduce the amount of intra- and inter-observer variability in determining an objective tumor response.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF DRAWINGS

In order to describe the manner in which the above recited and other advantages and features of the invention can be obtained, a more particular description of the invention briefly described above will be rendered by references to specific embodiments thereof, which are illustrated in the appended drawings. Furthermore, multiple instances of an element may each include separate letters appended to the element number. For example two instances of a particular element "200" may be labeled as "200a" and "200b". In that case, the element label may be used without an appended letter (e.g., "200") to generally refer to every instance of the element, while the element label will include an appended letter (e.g., "200a") to refer to a specific instance of the element. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
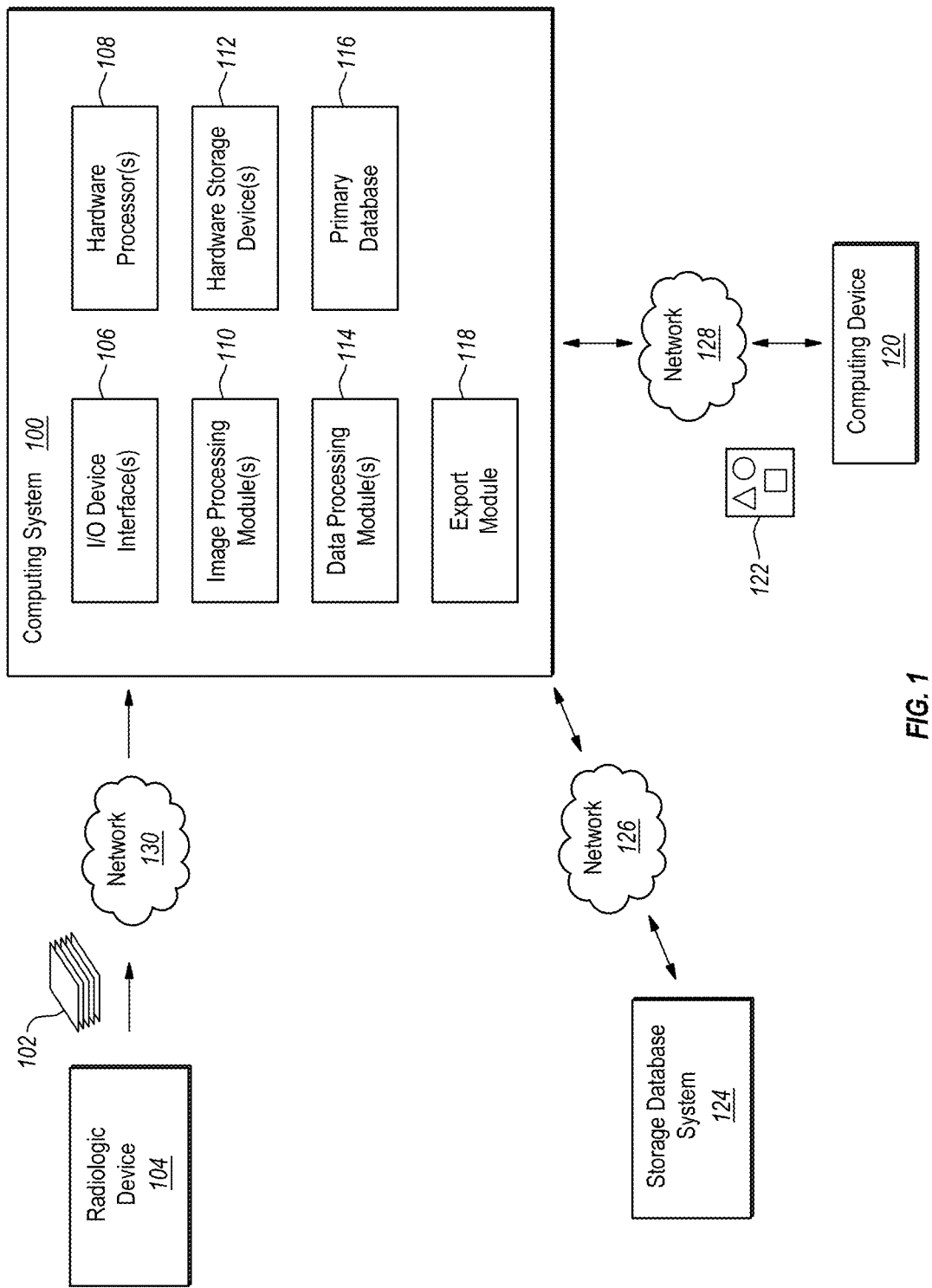
FIG. 1 is a schematic representation of a system for determining an objective tumor response to an anti-cancer therapy using one or more cross-sectional images according to one or more embodiments of the present disclosure.

While the detailed description is separated into sections, the section headers and contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, modules, devices, methods, and/or terminology.

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Overview of Imaging Evaluation of Tumor Response and Use of Tumor Response Criteria Imaging evaluation of tumor response to therapy is important for clinical trials and new drug development and routinely used for managing patients with advanced malignancies. Radiologic cross-sectional imaging is frequently used in oncologic clinical trials and in routine patient management regimens as a means of noninvasively evaluating response to therapy.

Traditional methods for assessing tumor response are based on measurements of target lesion length on radiologic cross-sectional images. The most commonly used tumor response assessment criterion is Response Evaluation Criteria In Solid Tumors (RECIST). RECIST 1.0 was originally developed in the year 2000 to evaluate solid tumor response to cytotoxic chemotherapy but was simplified and improved in the year 2009, resulting in RECIST 1.1. The improved RECIST 1.1 tumor response criterion serves as a longitudinal tumor response assessment tool that allows the treating oncologic provider to assess disease severity over time and to make better-informed anti-cancer treatment recommendations.

In order to perform RECIST 1.1, a user must strictly adhere to a number of rules and steps, some of which guide target lesion selection, measurement, and assessment. RECIST 1.1 also provides a number of mathematical, data transfer, and recording steps. This criterion assesses the tumor burden at two or more time points, and the final classification of tumor response to therapy is based on changes in the tumor burden, response of non-target lesions to therapy, and the presence or absence of new metastases. An error in any step may lead to an incorrect classification of tumor response to therapy, which could negatively impact patient care, quality of life, and survival. Common errors include selecting target lesions that do not meet RECIST 1.1 standards, measurement errors, data transfer errors, mathematical errors, and tumor response classification errors.

In the last decade, a number of new anti-cancer therapies have been developed, including new targeted agents, immunotherapies, ablative therapies, embolization therapies, and radiotherapies. While the mechanism of action for each of these therapies may be unique, there are several commonalities between them. The overwhelming majority of tumors require a vascular supply to remain viable or to grow. Many newer therapies disrupt tumor vascularity, either at macro- or micro-vessel level, and directly or indirectly cause tumor devascularization. Collectively, these therapies can be considered anti-angiogenic (AAG). AAG therapies are used to treat metastatic disease emanating from all major tumors, including: lung, breast, prostate, colon, renal cell carcinoma (RCC), hepatocellular carcinoma (HCC), melanoma, and many others.

Many effective anti-angiogenic therapies do not cause significant decreases to tumor length when viewed by radiologic cross-sectional images, and RECIST 1.1, thereby, underestimates tumor response to AAG therapy. A successful AAG therapy results in tumor devascularization, which can lead to moderate tumor shrinkage and/or marked changes in vascularity as reflected by a decrease in tumor attenuation or visible signs of necrosis on contrast-enhanced CT images.

The ideal tumor imaging biomarker for patients with advanced cancer treated by AAG therapy could be used both as a longitudinal tumor response assessment tool and used to predict response to a AAG therapy after one cycle of therapy. The ideal tumor imaging biomarker could be a straightforward quantitative metric or set of metrics that is or are directly related to the main effect of AAG therapy, namely tumor devascularization. Further, such an ideal tumor response criterion could be easy to use, widely available, widely applicable, amenable to high throughput, inexpensive, and highly reproducible across multiple different institutions and readers.

However, the currently available tumor response criteria do not meet the foregoing characteristics of an ideal tumor response criterion. All current genetic and serum biomarkers have insufficient accuracy for clinical use, and none have been externally validated. A variety of imaging biomarkers are under development, including positron emission tomography fused with computed tomography images (PET CT), computed tomography perfusion (CTP) imaging, advanced magnetic resonance imaging (MRI) techniques, and post-processing techniques for routine contrast-enhanced computed tomography (CT).

Evaluation of glucose metabolism by fluorodeoxyglucose (FDG) PET CT does not predict response to AAG. Newer PET radiotracers that evaluate specific angiogenesis pathways have failed in clinical trials to predict outcomes and to serve as a useful biomarker. CT perfusion is technically challenging, is semi-objective, is performed differently by each manufacturer, is not reproducible on different scanners or at different institutions, is not widely available, requires large amounts of processing time (not conducive to clinical workflow), and is only able to evaluate large tumors in a single body region (not the entire body in patients with diffuse metastatic disease). Advanced MRI techniques are not reproducible between different scanners or institutions and cannot be used to evaluate small lung metastases.

On the other hand, CT imaging is widely available, amenable to high throughput, reliable, inexpensive, and reproducible across multiple centers, making routine contrast-enhanced or unenhanced CT images the most promising imaging technique to serve as a foundation for generating surrogate biomarkers for tumor response to AAG therapy. The general purpose of CT imaging is to follow tumor size changes over time. However, AAG therapy frequently fails to shrink tumors early in the course of therapy, so reliance upon size measurements alone to indicate response to AAG therapy is insufficient to serve as a surrogate biomarker for tumor response or survival. Thus, post-processing of CT images may hold some promise for identifying surrogate biomarkers for tumor response to AAG therapy.

Newer CT imaging criteria have been developed to assess tumor response to AAG therapy, including Morphology Assessment Size and Structure (MASS) Criteria. MASS Criteria includes evaluation of contrast-enhanced CT images for the presence or absence of marked central necrosis, defined as greater than 50% (as subjectively determined by the user) of the enhancing central portion of a predominantly solid mass subjectively changing to near fluid attenuation (necrosis) after treatment. In addition, MASS Criteria includes evaluation for changes in tumor size (using single slice length measurements of target lesions) and changes in tumor attenuation. In applying MASS Criteria, the user assesses for marked decreased attenuation in one or more target lesions, referring to one or more target lesions showing a greater than 40 Hounsfield Unit (HU) decrease in mean attenuation following AAG therapy, as compared to baseline pre-therapy contrast-enhanced CT imaging.

Another commonly used CT imaging criteria for assessing tumor response to AAG includes Choi Criteria, which is most commonly used in metastatic gastrointestinal tumor treated with AAG therapy. Choi Criteria includes evaluation for changes in tumor size (using a single slice length measurement of target lesion) and changes in mean tumor attenuation. For Choi Criteria, the mean attenuation of each target lesion in Hounsfield Units is measured, and an arithmetic mean of all target lesions is used to calculate the final mean tumor attenuation. If the overall decrease in the final mean tumor attenuation is >15% compared to the baseline pre-therapy CT scan, then the patient is said to have had a Partial Response to therapy.

Both MASS Criteria and Choi Criteria utilize routine contrast-enhanced CT images for tumor response assessment to AAG, and contrast-enhanced CT imaging is widely available and commonly used in the assessment of these patients. Furthermore, the strength in these newer CT imaging criteria is that they utilize multiple CT imaging findings to evaluate tumor response to AAG therapy, thereby better predicting tumor response to AAG therapy than by evaluation of tumor size alone, such as per RECIST.

Tumor enhancement or attenuation on contrast-enhanced CT images is related to tumor vascularity, and both MASS Criteria and Choi Criteria include measurements of mean tumor attenuation, though objective tumor response is defined differently. There is little to no additional expense and no additional radiation required to make the tumor size or mean attenuation measurements. The process of making these measurements is standardized and relatively easy to do with most picture archiving and communications systems. MASS Criteria is perhaps further strengthened because it is includes evaluation for development of tumor necrosis, a natural consequence of successful AAG therapy.

However, neither MASS Criteria nor Choi Criteria is the solution to the lack of an ideal response criterion for determining and predicting tumor response to AAG therapy. A weakness of MASS Criteria is that assessment for marked tumor necrosis is subjective and thereby subject to reduced reproducibility. The weaknesses of both MASS Criteria and Choi Criteria are that tumor vascularity is assessed by measuring changes in the mean tumor attenuation of target lesions on contrast-enhanced CT images. The intensity, or mean tumor attenuation, on contrast-enhanced CT is related to the amount of tumor vascularity, but the mean attenuation and enhancement of target lesions is also related to the amount of administered intravenous iodinated contrast, the rate of injection of contrast, cardiac output, and numerous CT scan parameters (e.g., kVp, mAs or mA, smoothing kernel, etc.). In addition, inadvertent inclusion of adjacent structures or tissues may skew the mean intensity value, such as inclusion of lung tissue in a region of interest around a lung nodule. Both MASS Criteria and Choi Criteria measure the intensity of enhancement, but neither quantifies the amount of enhancing tissue.

In recent years, investigators have explored CT texture analysis. While this technology can have different meanings, current forms of this technology objectively quantify overall pixel intensity and/or tumor heterogeneity. Common metrics used include mean, mean positive pixels, standard deviation, entropy, kurtosis, and skewness of target lesions. Each of the foregoing parameter can be measured before and after processing the images with spatial band-pass filters having different bandwidths. These methods are highly quantitative, but their ability to predict tumor response to AAG therapy is limited, and the biologic mechanism linking CT texture analysis to tumor response to AAG therapy is not understood. It is also unclear how measurements of multiple tumors should be combined to indicate a final response to AAG therapy.

Both MASS Criteria and Choi Criteria and CT texture analysis fail to directly quantify the amount of enhancing tumor (also known as the vascular tumor burden), and prior to this application, there were no methods to directly quantify the vascular tumor burden from CT images. Tumors have both vascular components and avascular (necrotic) components. The component of tumor that is vascularized enhances, while the avascular portion does not and may be fluid density or have low attenuation. The vascular tumor burden is thought to significantly decrease in response to successful AAG therapy, though the total tumor size often does not. Furthermore, an increase in vascular tumor burden may be a better indicator of AAG therapy, as it has the potential to provide a quicker determination of AAG failure than waiting for new metastases or an increase in total tumor size by >20%. Prior to this application, there were no methods to directly quantify the vascular tumor burden prior to or after AAG therapy. There were also no methods to simultaneously assess one or more tumor metrics as defined by any combination of the known tumor response criteria, including RECIST, Choi Criteria, MASS Criteria, and CT texture analysis, while employing methods to reduce errors in tumor assessment and reduce the overall time of interpretation compared to serial tumor assessment by the various criteria and CT texture analysis.

In clinical trials, it is often necessary to evaluate patients by a variety of imaging-based tumor response criteria. As each criterion has different standards and methods, it is quite challenging to minimize errors when evaluating patients using one or more of the known imaging-based tumor response criteria. Furthermore, none of the existing tumor response criteria incorporate fully quantitative metrics that directly capture tumor devascularization, the main effect of anti-angiogenic therapy.

In clinical trials that include patients with advanced cancer treated with anti-angiogenic therapy, there is a need to simultaneously assess tumor response on cross-sectional images via a plurality of tumor response criteria. It is currently unclear which tumor response criterion is best for which tumor and which criterion is best paired with which anti-angiogenic therapy. Furthermore, there is a need to directly quantify changes in the vascular tumor burden on cross-sectional images to effectively monitor response to anti-angiogenic therapy and to predict long-term response to anti-angiogenic therapy.

Vascular Tumor Burden as a Tumor Response Criterion

The Vascular Tumor Burden (VTB) Criteria, as disclosed and enabled herein, fill the need for an ideal response criterion for determining and predicting tumor response to AAG therapy. As discussed below, the VTB Criteria provide a straightforward quantitative metric that is directly related to the main effect of AAG therapy, namely tumor devascularization, and is easy to use, is based on post-processing CT images, which makes it widely available, is widely applicable, is amenable to high throughput, is inexpensive, and is highly reproducible across multiple different institutions and readers.

In general, the VTB is defined by a quantitative measure of pixel intensity within a target lesion. More particularly, to determine VTB, the total range of pixel intensities for a given target lesion is determined and the range of pixel intensities is restricted to a first restricted range of pixel intensities, wherein the first restricted range of pixel intensities corresponds to a first subset of pixel intensities representative of vascularized tumor. Stated another way, deriving the VTB comprises determining an area (or volume) of pixels within the first restricted range of pixel intensities. For example, the restricted range of pixel intensities for a CT image may be from +40 to +300 HU for a solid metastasis or lymph node, -100 to +300 HU for a lung metastasis, or any range of pixel intensities. In fact, the range of pixel intensities used to define the vascular tumor burden may differ for unenhanced and contrast-enhanced images and may differ by location of the target lesions (e.g. liver versus lung).

For example, when injected radiocontrast is present in a CT image, the restricted range of pixel intensities may be defined from about +1 HU to about +500 HU or from about +80 HU to about +200 HU, more preferably from about +20 HU to about +450 HU or from about +20 HU to about +250 HU, from about +25 HU to about +400 HU or from about +30 HU to about +350 HU or from about +30 HU to about +200 HU or from about +50 HU to about +450 HU or from about +60 HU to about +480 HU, and most preferably from about +35 HU to about +325 HU or from about +40 HU to about +300 HU.

As a further example, when injected radiocontrast is absent from a CT image, the restricted range of pixel intensities may be defined from about +1 HU to about +500 HU or from about +1 to about +200 HU or from about +50 HU to about +200 HU, more preferably from about +5 HU to about +425 HU or from about +5 HU to about +225 HU, or from about +10 HU to about +400 HU or from about +10 HU to about +250 HU or from about +15 HU to about +350 HU or from about +40 HU to about +300 HU, and most preferably from about +20 HU to about +300 HU or from about +25 HU to about +275 HU.

The purpose of the restricted range of pixel intensities is to strictly define the vascular tumor burden and to exclude structures such as air, fat, fluid, necrotic tumor, nonenhancing tumor, dense calcification, intensely enhancing vascular structures, metal, foreign bodies and/or image artifacts that typically have pixel intensities above or below the specified range of pixel intensities designed to capture the VTB.

Accordingly, any conceivable range that effects that purpose is found to be within the scope of this disclosure.

By defining the VTB by the quantitative measure of a range of pixel intensities derived from post-processing digital radiologic cross-sectional images, the VTB can be determined easily, inexpensively, is widely available, is widely applicable, is amenable to high throughput, and is highly reproducible across multiple different institutions and readers. Further, the VTB can be leveraged in longitudinal studies to derive a decrease, increase, or no change in the vascularization of a given tumor, which may help to predict the tumor response to anti-cancer therapy, including AAG therapy.

Systems for Determining Objective Tumor Response

Referring now to FIG. 1, depicted is a schematic representation of a system for determining an objective tumor response to an anti-cancer therapy using one or more cross-sectional images according to one or more embodiments of the present disclosure. FIG. 1, generally, includes a computing system 100 configured to determine an objective tumor response. The computing system 100 may receive one or more cross-sectional images 102 from a radiologic device 104. In some embodiments, the radiologic device and the computing system are physically connected and the one or more cross-sectional images 102 are transferred via the physical connection. In other embodiments, the computing system 100 receives the one or more cross-sectional images 102 from the radiologic device 104 via a network 130 digitally connecting the radiologic device to the computing system 100. The network 130 may be a private network such as an intranet of a hospital or the network 130 may be a public network such as the Internet.

In some embodiments, the radiologic device comprises any device that generates one or more cross-sectional images obtained by at least one of: x-ray computed tomography, computed tomography perfusion (CTP) imaging, positron emission tomography (PET), single-photon emission computed tomography (SPECT), or magnetic resonance imaging (MRI). Consequently, in some embodiments, the one or more cross-sectional images comprise: CT images, CTP images, CAT scan images, PET images, SPECT images, or MRI images.

Upon receiving the one or more cross-sectional images 102, the computing system 100 may store the one or more cross-sectional images 102 in a primary database 116 or a hardware storage device 112 for later access or may process one or more of the of the one or more cross-sectional images 102. By processing any of the one or more cross-sectional images 102, the computing system 100 identifies one or more target lesions within the one or more cross-sectional images 102. The one or more target lesions are identified according to requirements disclosed by one or more predefined tumor response criteria stored within computing system 100. In some embodiments, the one or more predefined tumor response criteria may be user-defined, or it may be defaulted to a particular tumor response criterion such as, for example, the RECIST 1.1 Criteria. In yet other embodiments, the computing system 100 determines which tumor response criteria to use based on one or more data within the one or more cross-sectional images 102 such as, for example, the anatomical location represented in the one or more cross-sectional images 102 or by the presence or absence of injected radiocontrast in the one or more cross-sectional images 102.

Upon identifying the one or more target lesions from the one or more cross-sectional images 102, the computing system may, in some embodiments, select a particular slice for each of the one or more target lesions. The slice may be selected by, for example, determining the slice from the one or more cross-sectional images 102 where the given lesion has the longest length measurement. Other lesion characteristics may be used in selecting the slice, including, for example, the length of the short axis or the area of the lesion or the slice with the largest amount of vascular tumor. Selecting a particular slice for each of the one or more target lesions may be carried out by an image processing module 110 of the computing system 100 and may be done automatically or may be selected by a user through I/O device interface 106.

In some embodiments, the computing system 100 analyzes at least one of the one or more target lesions with an image processing module 110, wherein for the at least one of the one or more target lesions, the image processing module 110 is configured to perform one or more of the following: identify a total range of pixel intensities within the target lesion; restrict the total range of pixel intensities to a first restricted range of pixel intensities, wherein the first restricted range of pixel intensities corresponds to a first subset of pixel intensities representative of vascularized tumor; and determine one or more lesion metrics. In some embodiments, the image processing module 110 is configured to perform only two of the foregoing. In some embodiments, the image processing module 110 is specifically configured to identify a total range of pixel intensities within the target lesion and restrict the total range of pixel intensities to a first restricted range of pixel intensities.

In any of the foregoing embodiments where the image processing module 110 is configured to restrict the range of pixel intensities, the restricted range of pixel intensities may be set to any range of pixel intensities automatically determined by the computing system 100 or as directed by the user through I/O device interface 106. Additionally or alternatively, the restricted range of pixel intensities may be any of the ranges discussed above with respect to deriving the VTB and may be informed by one or more criteria such as anatomical location of the tumor or the presence or absence of injected radiocontrast.

In some embodiments, the computing system 100 compensates for the presence or absence of injected radiocontrast through, for example, image processing module 110, in any of the one or more cross-sectional images that comprise computed tomography images, the compensating comprising defining the first restricted range of pixel intensities to between about +40 and about +300 Hounsfield units when injected radiocontrast is present and defining the first restricted range of pixel intensities to between about +20 and about +300 Hounsfield units when injected radiocontrast is absent. The presence or absence of the radiocontrast may be automatically determined by the computing system 100 (e.g., the image processing module 110 or the data processing module 114 identifying one or more metadata associated with the one or more cross-sectional images being received at the computing system) or may, alternatively, be selected by a user at I/O device interface 106.

In some embodiments, the image processing module 110 determines one or more lesion metrics. In some embodiments, the one or more lesion metrics are selected by a user at a user interface, such as the I/O user interface 106 of computing system 100, and the image processing module 110 calculates and/or determines the user-specified lesion metrics for the at least one of the one or more target lesions. The one or more lesion metrics may include one or more lesion metrics selected from the group consisting of: a longest dimension length; a short axis dimension length; a longest dimension length of vascularized tumor; a pixel area of the at least one of the one or more target lesions; a pixel area within the first restricted range; a pixel area within the second restricted range; a mean value of pixel intensities within the total range of pixel intensities; a mean value of pixel intensities within the first restricted range of pixel intensities; a histogram parameter, wherein the histogram parameter comprises a quantitative distribution of pixel intensities in the at least one of the one or more target lesions; and a texture parameter, wherein the texture parameter comprises a geographic distribution of pixel intensities in the at least one of the one or more target lesions.

In some embodiments, the image processing module 110 or the computer system 100, generally, may additionally be configured to: restrict the total range of pixel intensities to a second restricted range of pixel intensities, wherein the second restricted range of pixel intensities corresponds to a second subset of pixel intensities representative of avascular (or necrotic) tumor; and derive a necrotic tumor burden for the at least one of the one or more target lesions, wherein deriving the necrotic tumor burden comprises determining an area or volume of pixels within the second restricted range of pixel intensities.

Restricting the total range of pixel intensities to a second restricted range of pixel intensities may include analogous compensation by the computing system based on the presence or absence of injected radiocontrast when restricting the first range of pixel intensities. Additionally or alternatively, the second restricted range of pixel intensities may not overlap with the first restricted range of pixel intensities or may overlap by about 1, 3, 5, 7, 10, 15, 20, 40, or 80 HU on either the upper and/or lower bound of the first restricted range. Additionally or alternatively, the second restricted range may only restrict the pixel intensities falling at or below the lower bound of the first restricted range. For example, if the first restricted range is between about +40 HU and about +300 HU, then the second restricted range may only restrict a subset (or the whole range) of HU values at or below about +40.

In some embodiments, analyzing the at least one of the one or more target lesions with an image processing module comprises analyzing a first cross-sectional image and a second cross-sectional image of the at least one of the one or more target lesions, wherein the first cross-sectional image comprises digital medical image data of the at least one of the one or more target lesions captured at a first point in time and the second cross-sectional image comprises digital medical image data of the at least one of the one or more target lesions captured at a second point in time, the second point in time being chronologically after the first point in time; and evaluating the second cross-sectional image with respect to the first cross-sectional image.

Having a temporal comparison between the at least one of the one or more target lesions (and any other target lesion) allows for changes in metrics to be computed which detail changes in one or more lesion metrics over time. These data may be informative in concluding whether a therapy is working. For example, if the change in data indicates that the area of a lesion is less at the second time point when compared to the first time point, it may indicate that the whole tumor or a component of the tumor (e.g., the vascular tumor burden) is shrinking and that the therapy is working. While not indicative, the data may, nonetheless, be informative.

In some embodiments, the computing system 100 of FIG. 1 may further derive a vascular tumor burden for the at least one of the one or more target lesions. This may be accomplished, for example, by data processing module 114, where the pixel area in the first restricted range is calculated and provided as a quantitative indication of VTB. Additionally or alternatively, the computing system 100 may derive a necrotic tumor burden for the at least one of the one or more target lesions. The second restricted range of pixel intensities may be used to define a necrotic tumor burden in an analogous fashion to how a VTB is determined using the first restricted range of pixel intensities. That is, in some embodiments, the area (or volume) of pixel intensities within the second restricted range of pixel intensities may be used to derive a necrotic tumor burden, which can similarly be calculated at data processing module 114 of computing system 100.

In either of the foregoing instances—deriving the vascular tumor burden or deriving the necrotic tumor burden—each may be accomplished within computing system 100 by one or more hardware processors 108 and/or by a data processing module 114 and may be derived in any manner or analogous manner previously described above for defining and/or determining the VTB.

In some embodiments, the computing system 100, whether through hardware processor 108 or data processor module 114, or a combination thereof, determines the objective tumor response for the at least one of the one or more target lesions wherein the objective tumor response is based on the vascular tumor burden. In some embodiments, therefore, comparative measures of the VTB at different time points may be used to determine the objective tumor response. In other embodiments, the objective tumor response for the at least one of the one or more target lesions may be based on the VTB and one or more tumor response criteria, as defined herein. That is, in some embodiments, the objective tumor response may be the resultant combination of tumor response criteria. In yet other embodiments, the objective tumor response is based on one or more tumor response criteria, wherein the one or more tumor response criteria comprise the one or more tumor response criteria as defined herein.

Importantly, and as will be described in greater detail with respect to various disclosed methods, determining the objective tumor response and any of the other disclosed derivations, determinations, or analyses performed in embodiments disclosing the computing system 100 of FIG. 1 may be done automatically by the computing system, may be performed after receiving one or more user instructions at a computer interface, or may be performed as a combination thereof. In some embodiments, the computer acts as a guide for the user, leading the user to determining an objective tumor response from one or more cross-sectional images and preventing errors in target lesion selection, data transfer, mathematical processing, response classification, and data and image archival. In other embodiments, the computing system automatically computes and derives data such as one or more of the vascular tumor burden, the necrotic tumor burden, and the objective tumor response. The computing system may, in some embodiments, automatically calculate or determine a plurality of tumor response criteria and may selectively, reiteratively, or automatically calculate any lesion metrics, tumor response criteria, VTB, or other data in response to a user editing or changing one or more criteria at a user interface.

Some distinct advantages of automating the process of determining an objective tumor response is that it reduces the likelihood of human error, increases reproducibility, and provides a quantitative measure for certain tumor response criteria, such as the VTB Criteria, that would otherwise be left to subjective guesswork. Further, computer automation allows for simultaneous measurement of a plurality of tumor metrics (including VTB), simultaneous assessment of lesions by multiple tumor response criteria, reduced read times, automated mathematical calculations of summary data, automated generation of key images, automated archiving of regions of interest data, automated archiving of tumor metric data, and instant generation of a summary report.

The latter two elements will now be discussed with continued reference to FIG. 1. In some embodiments, one or more data determined, derived, and/or analyzed at computing system 100 may be exported by export module 118 and archived in a storage database system 124, wherein storage database system 124 comprises persistent memory. The storage database system 124 may be remote from the computing system such that send the one or more data to be archived at storage database 124 may necessitate transferring the data over a network 126. The network 126 may be the same network as networks 128 and 130, but in some embodiments, it is a different network.

For example, in some embodiments, the computer system, such as computer system 100, may also include computer executable instructions that are executable by one or more processors to configure the computer system to export and store the following in a database having persistent memory, similar to storage database 124: one or more data representing the one or more of lesion metrics and the determined objective tumor response; one or more cross-sectional images comprising the one or more target lesions, wherein the one or more cross-sectional images are exported as one or more portable network graphics files; and one or more data comprising the one or more target lesions, wherein the one or more data are exported in a Digital Imaging and Communications in Medicine (DICOM) format.

In some embodiments, the export module 118 exports data in specific formats as exemplified by the foregoing. However, in some embodiments, image files may be exported in any of a user-defined image file format, including without limitation, JPEG, TIFF, GIF, BMP, SVG, or other image file formats known in the art, or as a graphic file format such as, for example, PDF. Similarly, data comprising the one or more target lesions may be exported in any of text formats, image formats, graphic file formats, or any other suitable file format known in the art.

In some embodiments, the export module 118 exports at least a portion of the data from computing system 100 to any of storage database system 124, primary database 116, and/or directly to a user through I/O device interface 106. In some embodiments, export module exports key images and essential data upon user-termination of a session with computing system 100. Key images include any graphic or illustrations, as described in more detail below, generated as a result of determining an objective tumor response at computing system 100. Essential information includes any information generated as a result of determining an objective tumor response at computing system 100 and includes at least any of the following: one or more target lesions, identification labels for the one or more target lesions, derived VTB, determined objective tumor response, values indicating a first and/or a second restricted range of pixel intensities, and one or more determined lesion metrics. In some embodiments the user may select at a user interface what information is essential information and what information and/or key images will be exported and stored.

In some embodiments, the exported data in storage database system 124 may be compiled for statistical analysis to, for example, help inform future treatment strategies. In some embodiments, the data, when exported by export module 118, encrypts the data to protect any confidential patient information and may provide the user with a key, decryption algorithm, or the like to access the data at a later time. Additionally or alternatively, the data may be anonymized, removing any patient specific identification from the exported data before storing in a database or exporting to a user.

In any of the foregoing embodiments described with respect to FIG. 1, and other additional embodiments of the present disclosure, a user may access computing system 100 for determining an objective tumor response to an anti-cancer therapy from computing device 120 and may do so through I/O device interface 106 of the computing system 100. The user may access computing system 100 over network 128, which may be the same or a different network than those described for networks 126 and 130.

In one embodiment, the computing device and the computing system are the same. This may, for example, occur when one or more method steps embodied by one or more portions of FIG. 1 and its accompanying description provided herein comprise a computer programmable product.

In some embodiments, the user may interact with computing system 100 before, during, and/or after the computing system is determining an objective tumor response to an anti-cancer therapy using owe or more cross-sectional images. In doing so, the computing system 100 may also include computer executable instructions that are executable by one or more processors to configure the computer system to receive one or more inputs, wherein the one or more more inputs comprise: a determination of injected radiocontrast in any of the one or more cross-sectional images; data related to a response of one or more non-target lesions; a presence of one or more new metastases; a label for the at least one of the one or more target lesions, wherein the label comprises information selected from the group consisting of: a lesion type of the at least one of the one or more target lesions, wherein lesion type can be a primary tumor, metastasis, or lymph node; an anatomical location of the at least one of the one or more target lesions; and any combination thereof; and a label for the one or more non-target lesions, wherein the label comprises information selected from the group consisting of: a lesion type of the one or more non-target lesions, an anatomical location of the one or more non-target lesions, and any combination thereof.

The user may interact with the computing system 100 of FIG. 1 and receive a customizable summary image 122 from computing system 100. For the purposes of this disclosure a customizable summary image 122 is synonymous and interchangeable with a detailed summary display 122. The customizable summary image may comprise a first illustration, wherein the first illustration comprises an illustration of the at least one of the one or more target lesions at the first point in time, and a second illustration, wherein the second illustration comprises an illustration of the at least one of the one or more target lesions at the second point in time; and at least one additional component selected from the group consisting of: a third illustration, wherein the third illustration comprises an illustration of the vascular tumor burden at the first point in time; a fourth illustration, wherein the fourth illustration comprises an illustration of the vascular tumor burden at the second point in time; a fifth illustration, wherein the fifth illustration comprises an illustration of the necrotic tumor burden at the first point in time; a sixth illustration, wherein the sixth illustration comprises an illustration of the necrotic tumor burden at the second point in time; a seventh illustration, wherein the seventh illustration comprises an illustration of a total tumor burden at the first point in time; an eighth illustration, wherein the eighth illustration comprises an illustration of the total tumor burden at the second point in time; a first graphical display illustrating one or more changes in vascularized tumor between the first point in time and the second point in time; a second graphical display illustrating one or more changes in necrotic tumor between the first point in time and the second point in time; a numeric value representing at least one of a percent change, an average change, or an absolute change in the one or more lesion metrics; a first indication of objective response, wherein the first indication comprises an indication that the at least one of the one or more target lesions is responding or not responding to anti-cancer therapy; a second indication of objective response, wherein the second indication of objective response comprises an indication that the one or more non-target lesions is responding or not responding to anti-cancer therapy; a first readable text, wherein the first readable text comprises the one or more lesion metrics; a second readable text, wherein the second readable text comprises the presence or absence of new metastases; a third readable text, wherein the third readable text comprises the vascular tumor burden for the at least one of the one or more target lesions; a fourth readable text, wherein the fourth readable text comprises the necrotic tumor burden for the at least one of the one or more target lesions; and a fifth readable text, wherein the fifth readable text comprises the objective tumor response for the one or more target lesions as determined by the one or more tumor response criteria.

In some embodiments, the determination of which of the foregoing additional components will be displayed at the first illustration in the second illustration in the customizable summary image is dependent upon computing device 100. For example, computing device may have a standard and/or pre-determined display comprising one or more additional components. A user may, before or after viewing the customizable summary image adjust and/or customize the image to suit their needs.

While FIG. 1 depicts several independent modules 106, 108, 110, 114, 116, 118, one will understand the characterization of a module is at least somewhat arbitrary. In at least one implementation, the modules 106, 108, 110, 114, 116, 118 of FIG. 1 may be combined, divided, or excluded in configurations other than that which is shown. As used herein, the individual modules 106, 108, 110, 114, 116, 118 are provided for the sake of clarity and explanation and are not intended to be limiting.

Figure 2:
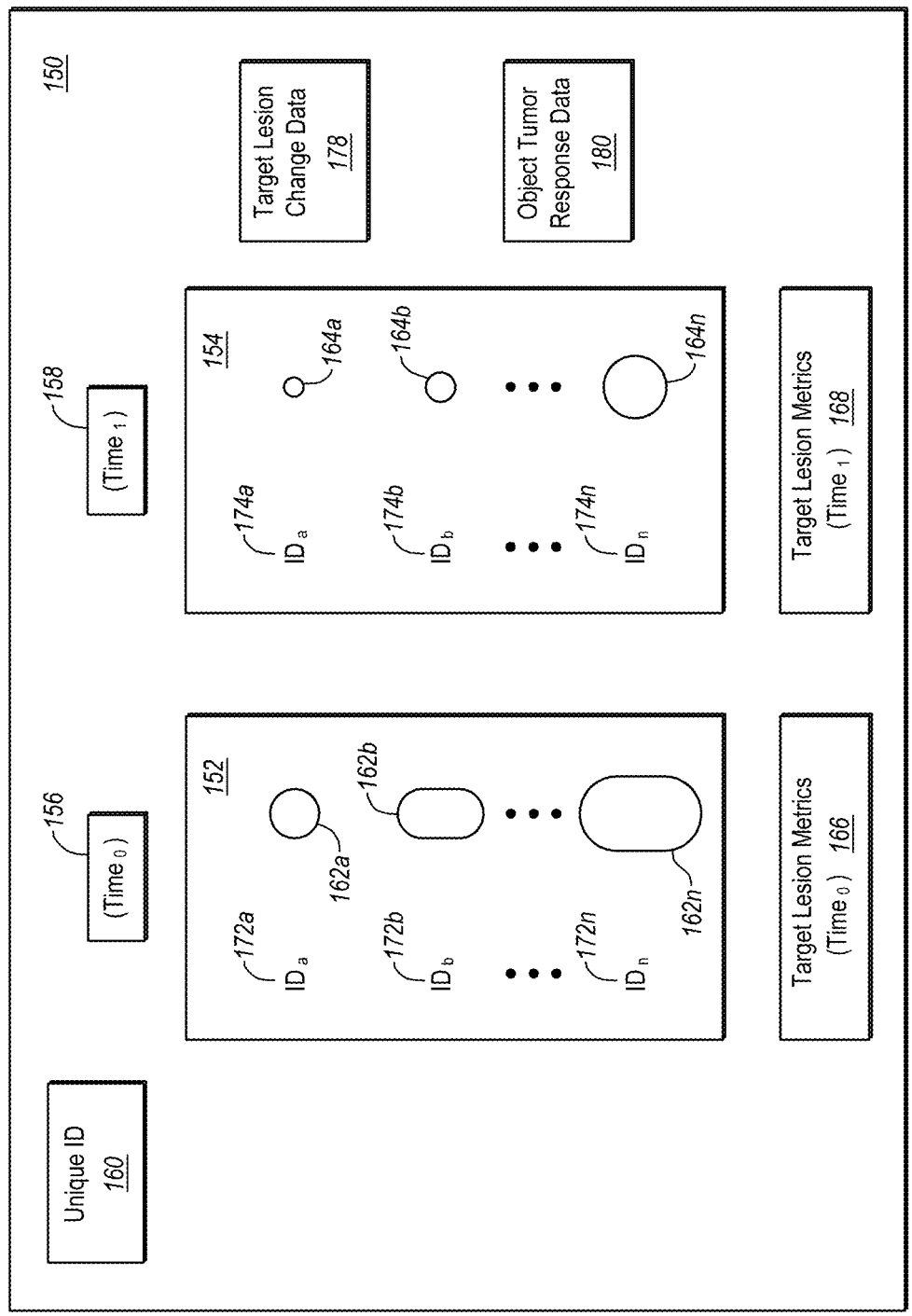
FIG. 2 is a schematic representation of a computer interface comprising a customizable summary image according to one or more embodiments of the present disclosure.
Figure 3:
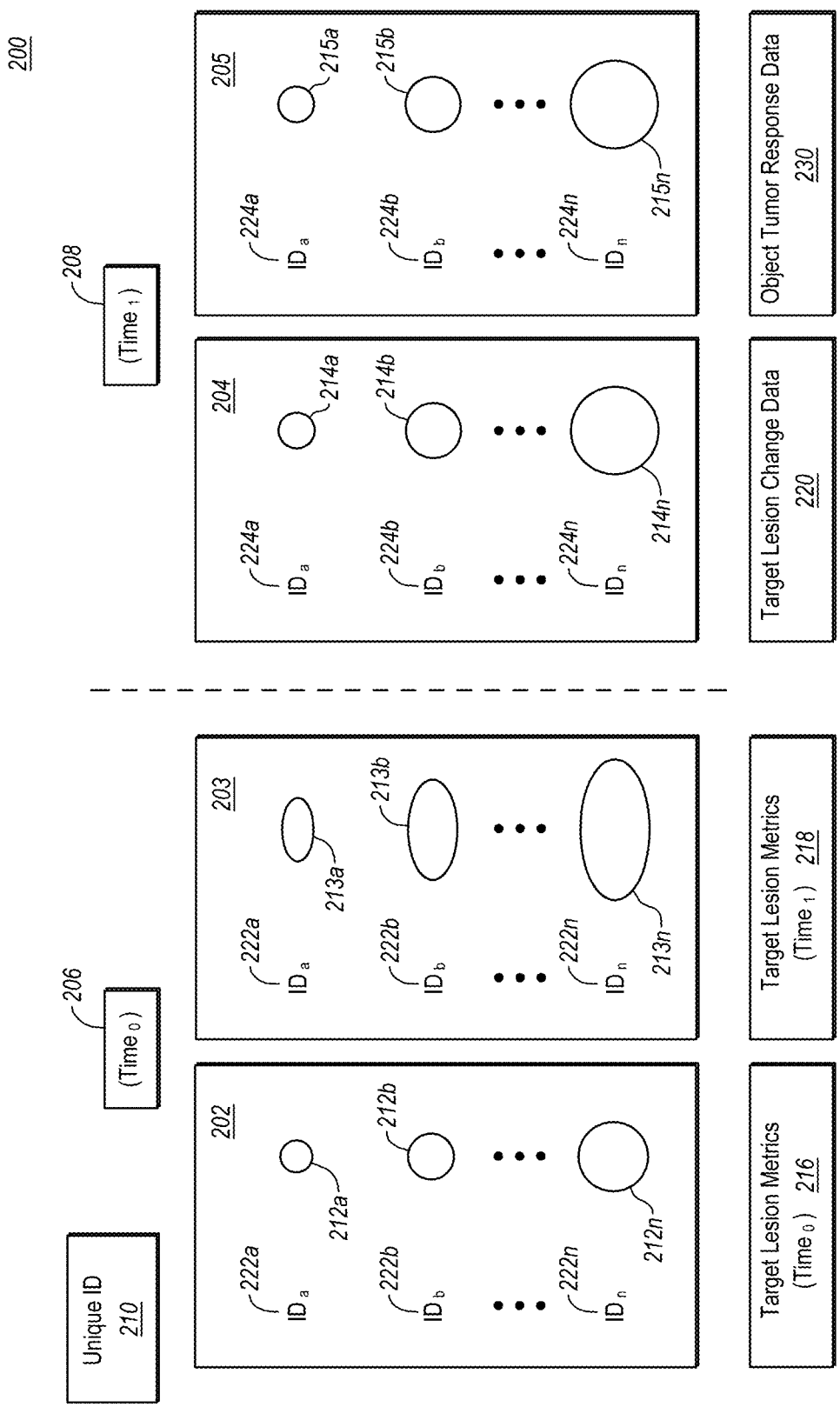
FIG. 3 is a schematic representation of a computer interface comprising a customizable summary image according to one or more embodiments of the present disclosure.

Referring now to FIGS. 2-5, illustrated are embodiments of computer interfaces comprising a customizable summary image according to one or more embodiments of the present disclosure. FIGS. 2-3 illustrate schematic representations of the actual embodiments of customizable summary images depicted in FIGS. 4-5, respectively.

FIG. 2 illustrates a computer interface comprising a customizable summary image 150. Included therein are a first illustration 152 and a second illustration on 154, where in the first illustration comprises at least one of the one or more target lesions 162. As depicted, there are at least three target lesions 162a, 162b, and 162n, where n is an integer greater than 2. Though depicted as at least three target lesions, it will be appreciated that the first illustration may depict as few as one target lesion and that the number of target lesions in the second illustration may be greater or less than the target lesions in the first illustration. If new metastases arise between the first and second point of time 156, 158, there may be a greater number of target lesions in the second illustration than in the first. If, however, the anti-cancer therapy is working, there may be two time points in the monitored therapy wherein the second illustration has fewer target lesions as compared to the first illustration due to a significant reduction in size of the tumor and/or destruction of the tumor.

Referring back to FIG. 2, each target lesion 162, 164 is associated with a label 172, 174 in so far that each of the target lesions depicted 162a, 162b, 162c, 164a, 164b, 164c is labeled respectively 172a, 172b, 172c, 174a, 174b, 174c. In some embodiments, label 172 is the same as label 174 because the second illustration 154 depicts the same target lesions illustrated in the first illustration 152, only a at a later point in time. In addition to the first and second illustrations 152, 154, the customizable summary figure 150 further includes target lesion metrics (Time0) 166, target lesion metrics (Time1) 168, target lesion change data 178, and objective tumor response data 180. The customizable summary figure 150 may also contain a unique ID 160, which may include patient identification information such as the patient's name, medical record number, date of birth, a coded identification number, or an anonymous patient ID number.

On the other hand, other embodiments of the present disclosure provide that the determination of which component(s) of the foregoing additional components will be displayed with the first illustration and the second illustration in the customizable summary image 122 is dependent upon one or more user selections at a user interface and/or at I/O device 106 of the computing system 100. The user may, in some embodiments, select one or two components, a plurality of components, or all of the components to be displayed with the first illustration and the second illustration in the customizable summary image 122.

Additionally or alternatively, the customizable summary image 122 may dynamically change as a user interacts with computing system 100 through a user interface, such as through I/O device interface 106. In some embodiments, the customizable summary image is a user interface and one or more of the displayed objects (e.g., objects associated with reference numbers 152, 154, 156, 158, 160, 162, 164, 166, 168, 178, 180) may be movable by the user from their current depicted position to a different position or they may be removed altogether. As a non-limiting example, the customizable summary image may include the third illustration overlain atop of the first illustration, and upon user selection through interface 106, the third illustration may be removed and replaced with a fifth illustration. The user may view this change in real time. Additionally or alternatively, the user may maintain the third illustration and add a fourth illustration to the customizable summary image. The computing system 100 is in many embodiments dynamically responsive to user inputs, and in doing so, outputs such as the customizable summary image 122 may be similarly dynamic in their displayed content. This gives the user, who may be a physician, the ability to explore various tumor response criteria and various lesion metrics as they relate to the one or more cross-sectional images. In this way, the physician's workload is streamlined, taking significantly less time to view and analyze imaging results, and enabling the physician to view a plurality of tumor response criteria simultaneously, including VTB, so a more-informed decision can be made with reference to the efficacy of the patient's therapy, which is particular useful with respect to patients undergoing AAG therapy.

Figure 4:
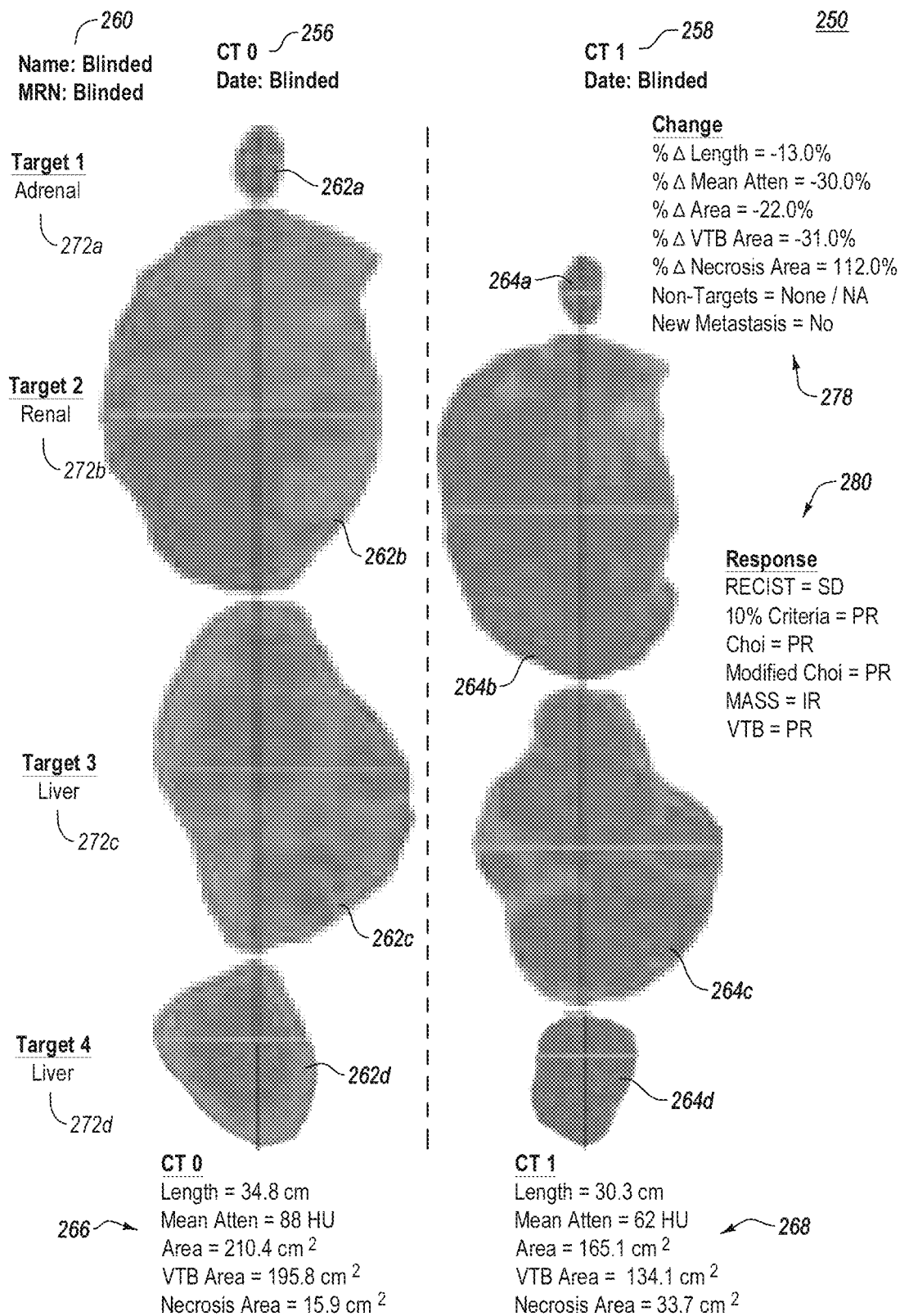
FIG. 4 depicts an implementation of the computer interface of FIG. 2 according to one or more embodiments of the present disclosure.

Referring now to FIG. 4, depicted is an implementation of the computer interface of FIG. 2. Depicted are four target lesions 262a, 262b, 262c, 262d at time point CT0 and the same four target lesions 264a, 264b, 264c, 264d at time point CT1. Each target lesion set includes target lesion metrics 266, 268 at each of the respective time points CT0 and CT1 and respectively represent a first illustration 256 and a second illustration 258. Also included in user interface/customizable summary image 250 are labels 272a, 272b, 272c, 272d indicating an anatomical location of the target lesion and providing a target number (e.g., Target 1, Target 2, etc.) as well as target lesion change data 278, which as depicted includes a percent change in: length, mean attenuation, total lesion area, VTB area, and necrosis area between target lesions at time points CT0 and CT1. Lastly, the customizable summary image 250 includes objective tumor response data 280, particularly, the objective tumor response data 280 include tumor response data from one or more tumor response criteria, namely RECIST, 10% Tumor Diameter Shrinkage Criteria (10% Criteria), Choi Criteria, Modified Choi Criteria, MASS Criteria, and VTB Criteria.

Similar to FIG. 2, in some embodiments, a user may dynamically change the order or layout of the customizable display image or may select different lesion metrics or different tumor response criteria to display.

Referring now to FIG. 3, depicted is a schematic representation of a computer interface comprising a customizable summary image 200 according to one or more embodiments of the present disclosure. FIG. 3 is similar to FIG. 2 and maintains some of the same items, such as: target lesion metrics (216 and 218, respectively for Time0 206 and Time1 208), target lesion change data 220, objective tumor response data 230, and a unique patient or customizable summary image ID 210. The main difference between FIG. 3 and FIG. 2 is the presence of additional illustrations for each time point. The first illustration 202 and second illustration 204 remain, and they maintain a similar temporal relationship as depicted in FIG. 2. Illustration 203 may be any of the third, fifth, or seventh illustrations and 205 may be any of the fourth, sixth, or eighth illustrations listed as one of the at least one additional component to accompany illustrations one and two in the customizable summary image. For each hypothetical pairing, the result is the same: illustration 203 depicts the same target lesions (i.e., 222a, 222b, 222n) at the same time point as those target lesions (212a, 212b, 212n) in the first illustration 202 but demonstrates those target lesions through the lens of VTB, necrotic tumor burden, or total tumor burden. For example, target lesion 212a is the same target lesion as target lesion 222a, but target lesion 212a shows the target lesion as originally captured from the one or more cross-sectional images, without any post-processing, whereas target lesion 222a shows target lesion 212a wherein some post-processing to the target lesion has taken place, perhaps being overlaid with a texture or color mask that depicts VTB.

The same or similar foregoing relationship may hold true for target lesions 214 and 215 of the second illustration 204 and illustration 205—which may be any one or more of the fourth, sixth, or eighth illustrations. Again, the texture and/or color associated with target lesions 215a, 215b, and 215n may be indicative of the VTB, necrotic tumor burden, or total tumor burden associated with target lesions 214a, 214b, and 214n, respectively.

Figure 5:
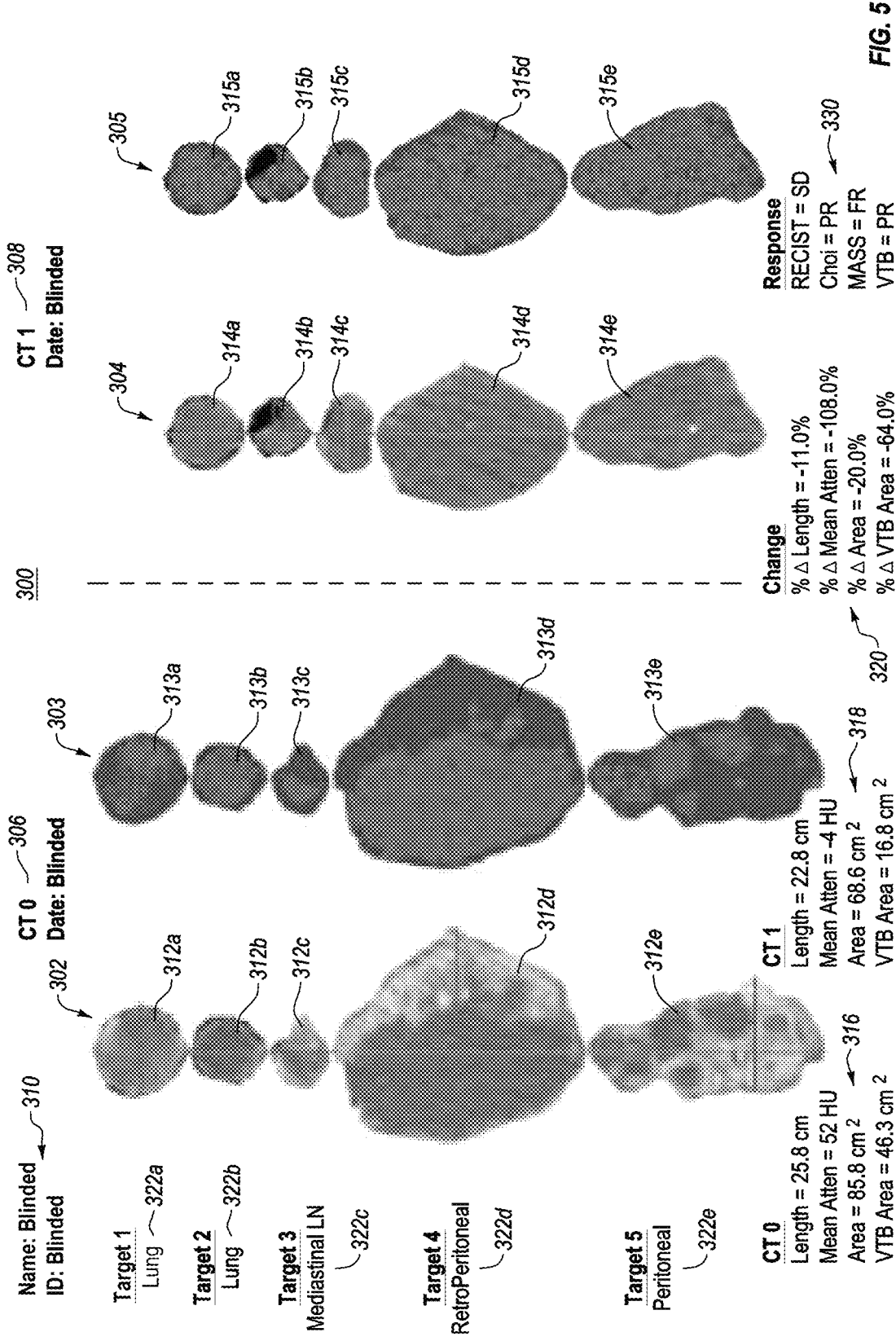
FIG. 5 depicts an implementation of the computer interface of FIG. 3 according to one or more embodiments of the present disclosure.

Referring now to FIG. 5, depicted is an implementation of the computer interface of FIG. 3 according to one or more embodiments of the present disclosure. FIGS. 3 and 5 maintain a similar relationship to that which was demonstrated above between FIGS. 2 and 4. With reference to FIG. 5, there are five target lesions depicted for each of the illustrations 302, 303, 304, and 305, each target lesion 312, 313, 314, 315 having a label 322a 322b, 322c, 322d, 322e that recites the anatomical location (e.g., lung, peritoneal, etc.) of the target lesion along with a target lesion ID (e.g., Target 1, Target 2, etc.). The abbreviation LN indicates that target lesion 322c is a lymph node, differentiating it from the other target lesions, which are metastases. Just as in FIGS. 2-4, FIG. 5 illustrates target lesion metrics 316, 318 for target lesions at respective time points CT0 and CT1 and target lesion change data 320, which as depicted includes a percent change in: length, mean attenuation, total lesion area, and VTB area between target lesions at time points CT0 and CT1. Lastly, the customizable summary image 300 includes objective tumor response data 330, particularly, the objective tumor response data 330 include tumor response data from one or more tumor response criteria, namely RECIST, Choi Criteria, MASS Criteria, and VTB Criteria.

Similar to FIGS. 2-4, in some embodiments, a user may dynamically change the order or layout of the customizable display image 300 of FIG. 5 or may select different lesion metrics 316, 318 or different tumor response criteria 330 to display.

Thus, implementations of the present invention may extend to computer systems comprising one or more computer readable hardware storage device that comprise computer executable instructions executable by at least one of one or more processors to cause the computer system to determine an objective tumor response to an anti-cancer therapy using one or more cross-sectional images. In particular, the computer systems may comprise computer-executable instructions that are executable by one or more processors to configure the computer system to perform the following: receive one or more cross-sectional images that comprise one or more cross-sectional slices of digital medical image data from a radiologic device; identify one or more target lesions within the one or more cross-sectional images; analyze at least one of the one or more target lesions with an image processing module, wherein for the at least one of the one or more target lesions, the image processing module is configured to: identify a total range of pixel intensities, restrict the total range of pixel intensities to a first restricted range of pixel intensities, wherein the first restricted range of pixel intensities corresponds to a first subset of pixel intensities representative of vascularized tumor, and determine one or more lesion metrics; derive a vascular tumor burden for the at least one of the one or more target lesions; and determine the objective tumor response for the at least one of the one or more target lesions wherein the objective tumor response is based on the vascular tumor burden.

Additionally or alternatively, implementations of the present invention may extend to computer systems comprising the foregoing computer system and which additionally comprises computer executable instructions executable by at least one of one or more processors to cause the computer system to select a slice from the one or more cross-sectional images for each of the one or more target lesions, wherein the slice selected for each of the one or more cross-sectional images comprises the slice having the longest dimension length for each of the one or more target lesions.

Additionally or alternatively, implementations of the present invention may extend to computer systems comprising one or more computer readable hardware storage device that comprise computer executable instructions executable by at least one of one or more processors to cause the computer system to perform the following: receive one or more cross-sectional images that comprise one or more cross-sectional slices of digital medical image data from a radiologic device; identify one or more target lesions within the one or more cross-sectional images; analyze at least one of the one or more target lesions with an image processing module, wherein for the at least one of the one or more target lesions, the image processing module is configured to: identify a total range of pixel intensities, restrict the total range of pixel intensities to a first restricted range of pixel intensities, wherein the first restricted range of pixel intensities corresponds to a first subset of pixel intensities representative of vascularized tumor, and restrict the total range of pixel intensities to a second restricted range of pixel intensities, wherein the second restricted range of pixel intensities corresponds to a second subset of pixel intensities representative of necrotic tumor; derive a vascular tumor burden for the at least one of the one or more target lesions; derive a necrotic tumor burden for the at least one of the one or more target lesions, wherein deriving the necrotic tumor burden comprises determining an area or volume of pixels within the second restricted range of pixel intensities; determine the objective tumor response for the at least one of the one or more target lesions, wherein the objective tumor response is based on the derived vascular tumor burden and one or more tumor response criteria; and provide a customizable summary image to one or more users, wherein the customizable summary image comprises a first illustration, wherein the first illustration comprises an illustration of the at least one of the one or more target lesions at the first point in time, and a second illustration, wherein the second illustration comprises an illustration of the at least one of the one or more target lesions at the second point in time; and at least one additional component selected from the group consisting of: a third illustration, wherein the third illustration comprises an illustration of the vascular tumor burden at the first point in time; a fourth illustration, wherein the fourth illustration comprises an illustration of the vascular tumor burden at the second point in time; a fifth illustration, wherein the fifth illustration comprises an illustration of the necrotic tumor burden at the first point in time; a sixth illustration, wherein the sixth illustration comprises an illustration of the necrotic tumor burden at the second point in time; a seventh illustration, wherein the seventh illustration comprises an illustration of a total tumor burden at the first point in time; an eighth illustration, wherein the eighth illustration comprises an illustration of the total tumor burden at the second point in time; a first graphical display illustrating one or more changes in vascularized tumor between the first point in time and the second point in time; a second graphical display illustrating one or more changes in necrotic tumor between the first point in time and the second point in time; a numeric value representing at least one of a percent change, an average change, or an absolute change in the one or more lesion metrics; a first indication of objective response, wherein the first indication comprises an indication that the at least one of the one or more target lesions is responding or not responding to anti-cancer therapy; a second indication of objective response, wherein the second indication of objective response comprises an indication that the one or more non-target lesions is responding or not responding to anti-cancer therapy; a first readable text, wherein the first readable text comprises the one or more lesion metrics; a second readable text, wherein the second readable text comprises the presence or absence of new metastases; a third readable text, wherein the third readable text comprises the vascular tumor burden for the at least one of the one or more target lesions; a fourth readable text, wherein the fourth readable text comprises the necrotic tumor burden for the at least one of the one or more target lesions; and a fifth readable text, wherein the fifth readable text comprises the objective tumor response for the one or more target lesions as determined by the one or more tumor response criteria.

As disclosed in the above system, implementations of the present disclosure may extend to systems for determining an objective tumor response to anti-cancer therapy that determine both a vascular tumor burden and a necrotic tumor burden and which require the objective tumor response to be determined by the vascular tumor burden and one or more tumor response criteria.

Additionally or alternatively, implementations of the present invention may extend to computer systems comprising one or more computer readable hardware storage device that comprise computer executable instructions executable by at least one of one or more processors to cause the computer system to perform the following: identify one or more target lesions within the one or more cross-sectional images; analyze at least one of the one or more target lesions with an image processing module, wherein for the at least one of the one or more target lesions, the image processing module is configured to: identify a total range of pixel intensities and restrict the total range of pixel intensities to a first restricted range of pixel intensities; derive a vascular tumor burden for the at least one of the one or more target lesions; and determine the objective tumor response for the at least one of the one or more target lesions, wherein the objective tumor response is based on the results from one or more tumor response criteria.

As noted in the foregoing computer system, implementations of the computer system falling within the scope of this disclosure include computer systems that determine the objective tumor response for at least one of the one or more target lesions, wherein the objective tumor response is based on the results from one or more tumor response criteria. The VTB may be included in the one or more tumor response criteria. In fact, the one or more tumor response criteria may be selected from the group consisting of: Response Evaluation Criteria in Solid Tumors (RECIST) 1.0, RECIST 1.1, modified RECIST, World Health Organization (WHO) Criteria, 10% Tumor Diameter Shrinkage Criteria, Choi Criteria, Modified Choi Criteria, Morphology Attenuation Size and Structure (MASS) Criteria, Immune-related Response Criteria, Cheson Criteria, lymphoma response criteria, Revised Response Criteria for Malignant Lymphoma, Positron Emission Tomography Response Criteria in Solid Tumors (PERCIST), Metabolic Response Criteria, European Organization for Research and Treatment of Cancer (EORTC), International uniform response criteria for multiple myeloma, Current Response Criteria for High-Grade Gliomas, MacDonald Criteria, Response Assessment of Neuro-Oncology (RANO) Criteria, Vascular Tumor Burden (VTB) Criteria, and computed tomography texture analysis criteria.

In some embodiments, a noise reduction filter may be applied to the digital medical image data and/or to any selected subset or portion thereof. Further, in some embodiments, a smoothing algorithm is applied to the digital medical image data. Moreover in some embodiments, the smoothing algorithm may be Gaussian, additive smoothing, butterworth filter, digital filter, kalman filter, kernel smoother, laplacian smoothing, stretched grid method, lowpass filter, local regression, smoothing spline, moving average, or exponential smoothing. In some embodiments, the smoothing algorithm comprises a Gaussian smoothing algorithm. In some embodiments, the smoothing algorithm is applied to the digital medical image data or to any portion thereof. In some embodiments, the smoothing algorithm is applied only to the region of interest. The sigma value for the Gaussian smoothing algorithm may be increased or decreased by the user, thereby increasing or decreasing the amount of smoothing, until the amount of smoothing is optimized. In other embodiments, other image processing algorithms may include a Fourier transformation of the image data or processing the data by point processing operations, spatial filter operations (linear or non-linear), histogram processing operations, contrast-stretching transformation, image logarithmic transformation, power law transformation, precise linear transformation, gray level slicing transformation, bit plane slicing, or pseudo coloring operations.

In some foregoing and forthcoming embodiments, the systems and methods of the present disclosure include a step deriving a VTB and/or extracting a VTB, wherein the VTB is defined as an area (or volume) of pixels within the first restricted range of pixel intensities in the digital medical image data. The step of deriving a VTB and/or extracting a VTB may include, for example, calculating a pixel value for each of the pixels in the first restricted range of pixel intensities from the digital medical image data and/or measuring a pixel value for each of the pixels in the first restricted range of pixel intensities from the digital medical image data.

Computer-Implemented Methods and Computer Interfaces for Determining Objective Tumor Response FIGS. 1-5 and the corresponding text illustrate or otherwise describe one or more components, modules, mechanisms and/or detailed summary displays (also referred to herein as customizable summary images) for determining an objective tumor response to an anti-cancer therapy using one or more cross-sectional images. One will appreciate that embodiments of the present invention can also be described in terms of methods comprising one or more acts for accomplishing a particular result. For example, FIGS. 6-10, with the corresponding text, illustrates or otherwise describes a sequence of acts in a method for determining an objective tumor response to an anti-cancer therapy using one or more cross-sectional images. The acts of FIGS. 6-10 are described below with reference to the components and modules illustrated in FIGS. 1-5.

Figure 6:
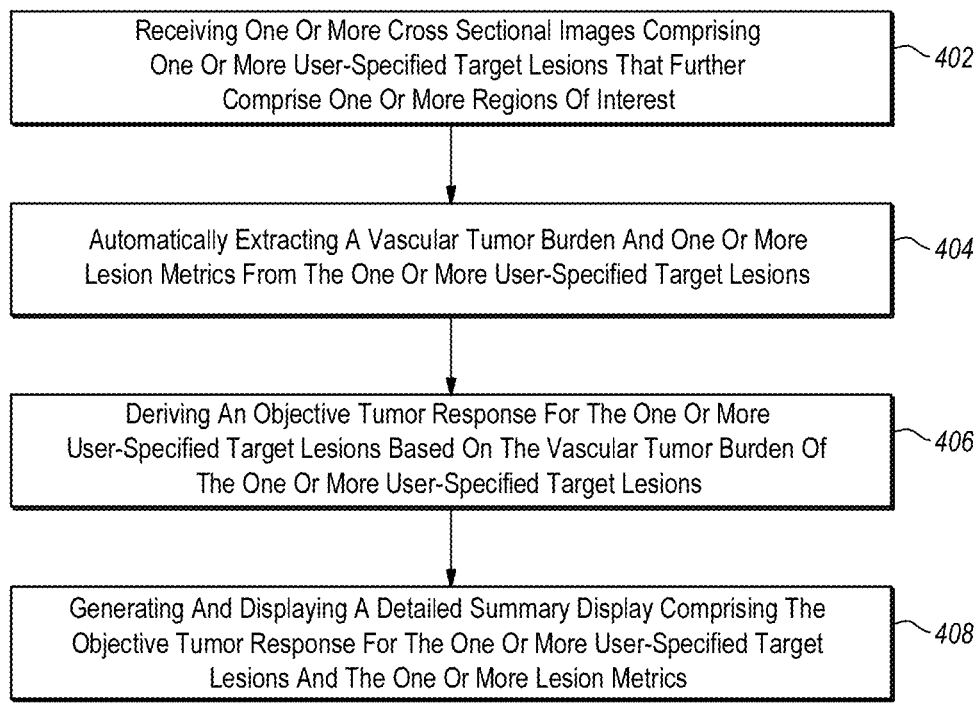
FIG. 6 illustrates a computer-implemented method of determining an objective tumor response to an anti-cancer therapy through user-interaction with a computer interface provided in accordance with one or more embodiments of the present disclosure.

FIG. 6 shows that a method 400 for generating and displaying a detailed summary display can include an act 402 of receiving one or more cross-sectional images comprising one or more user-specified target lesions that further comprise one or more regions of interest. Act 402 can comprise receiving one or more cross-sectional images, wherein the one or more cross-sectional images comprise one or more cross-sectional slices of digital medical image data from a radiologic device and identifying one or more target lesions within the one or more cross-sectional images. For example, computing system 100 of FIG. 1 may receive one or more cross-sectional images 102 from radiologic device 104, wherein the cross-sectional images 102 already include user-specified target lesions. Additionally or alternatively, a user may specify target lesions at computing system 100 through I/O device interface 106.

Additionally or alternatively, the cross-sectional images 102 comprising one or more user-specified target lesions may be received by computing system 100 from storage database system 124. In some embodiments, the one or more regions of interest within the user-specified target lesions may have been previously defined by a user and may include, for example, one or more restricted ranges of pixel intensities, whether chosen by a user or by a computing system.

FIG. 6 shows that the method 400 can also include act 404 of automatically extracting a vascular tumor burden and one or more lesion metrics from the one or more user-specified target lesions. Act 404 can comprise analyzing at least one of the one or more target lesions with an image processing module, wherein for the at least one of the one or more target lesions, the image processing module is configured to identify a total range of pixel intensities; restrict the total range of pixel intensities to a first restricted range of pixel intensities, wherein the first restricted range of pixel intensities corresponds to a first subset of pixel intensities representative of vascularized tumor; and determine one or more lesion metrics. Act 404 may further comprise deriving a vascular tumor burden for the at least one of the one or more target lesions.

In embodiments of the present invention, the image processing module 110 of computing system 100 may automatically extract a VTB and one or more lesion metrics from the one or more user-specified target lesions.

In addition, FIG. 6 shows that the method 400 can include act 406 of deriving an objective tumor response for the one or more user-specified target lesions based on the vascular tumor burden of the one or more user-specified target lesions. Act 406 can comprise determining the objective tumor response for the at least one of the one or more target lesions wherein the objective tumor response is based on the vascular tumor burden. In embodiments of the present invention, deriving an objective tumor response may be done by hardware processors 108, image processing modules 110, data processing modules 114, or any combination thereof, or by computing system 100, generally. It may further include or comprise deriving a VTB and/or extracting a VTB, using image processing module 114, wherein the VTB is defined as an area (or volume) of pixels within a first restricted range of pixel intensities in the one or more user-specified target lesions. Deriving a VTB and/or extracting a VTB may include, for example, the image processing module 110 calculating a pixel value for each of the pixels in the first restricted range of pixel intensities from the one or more user-specified target lesions and/or measuring a pixel value for each of the pixels in the first restricted range of pixel intensities from the one or more user-specified target lesions.

Furthermore, FIG. 6 shows that the method 400 can include act 408 of generating and displaying a detailed summary display comprising the objective tumor response for the one or more user-specified target lesions and the one or more lesion metrics. Act 406 can comprise displaying a customizable summary image, wherein the customizable summary image comprises a first illustration, a second illustration, and at least one additional component. For example, the detailed summary display (i.e., the detailed summary image) may be displayed at computing system 100 through I/O device interface 106 or may be transferred through network 128 to computing device 120, where a user may view the detailed summary image from a display associated with the computing device 120.

Figure 7:
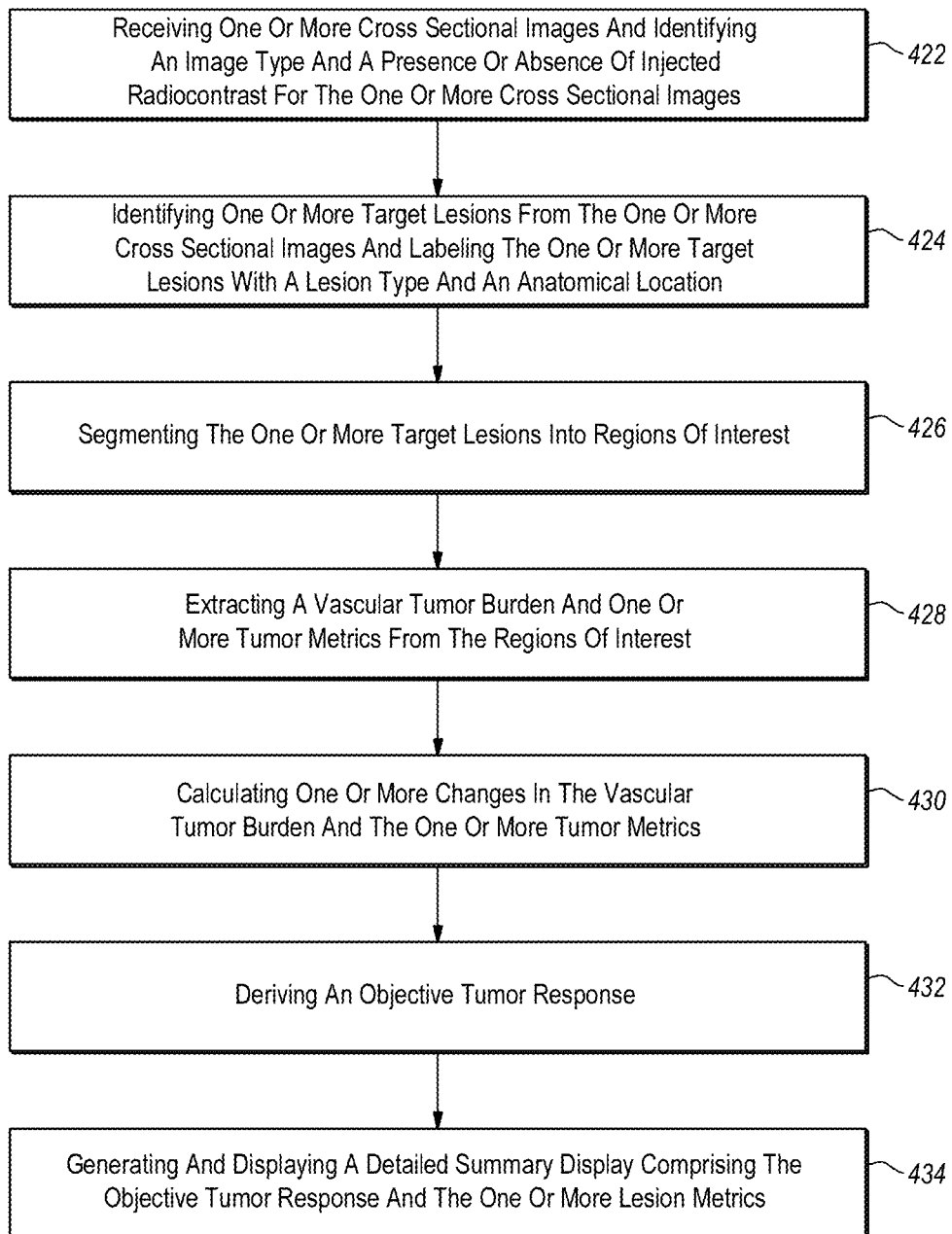
FIG. 7 illustrates a computer-implemented method of determining an objective tumor response to an anti-cancer therapy through user-interaction with a computer interface provided in accordance with one or more embodiments of the present disclosure.

Referring now to FIG. 7, FIG. 7 shows that the method 400 for generating and displaying a detailed summary display can include an act 422 of receiving one or more cross-sectional images and identifying an image type and a presence or absence of injected radiocontrast for the one or more cross-sectional images. Act 422 comprises receiving one or more cross-sectional images, wherein the one or more cross-sectional images comprise one or more cross-sectional slices of digital medical image data from a radiologic device, and receiving one or more inputs, wherein the one or more inputs comprise a determination of injected radiocontrast in any of the one or more cross-sectional images.

For example, the computing system 100 may receive one or more cross-sectional images 102 from radiologic device 104. The computing device may identify an image type and a presence or absence of injected radiocontrast from the one or more cross-sectional images 102 through an image processing module 110 that scans the one or more cross-sectional images 102 and makes a determination of the foregoing. Additionally or alternatively, computing system 100 may be pre-programmed to accept one or more cross-sectional images 102 from a particular radiologic device 104 such as, for example, CT images from a CT scanner, or computing system 100 may identify this information through data processing module 114, which reads one or more meta data tags associated with images 102 and which identify they type of image (e.g., a CT image, an MRI image, a PET image, a SPECT image, a CTP image, etc.) and the presence or absence of injected radiocontrast.

The method of FIG. 7 can also include an act 424 of identifying one or more target lesions from the one or more cross-sectional images and labeling the one or more target lesions with a lesion type and an anatomical location. Act 424 can comprise identifying one or more target lesions within the one or more cross-sectional images and receiving one or more inputs, wherein the one or more inputs comprise a label for the at least one of the one or more target lesions, wherein the label comprises information selected from the group consisting of: a lesion type of the at least one of the one or more target lesions, wherein lesion type can be a primary tumor, metastasis or lymph node; an anatomical location of the at least one of the one or more target lesions; and any combination thereof.

For example, an image processing module 110 of the computing system 100 may identify one or more target lesions from images 102 and a hardware processor 108 or data processing module 114 or a combination thereof may include one or more data with images 102 that comprise a label having information related to the lesion type and anatomical location of the one or more target lesions. In some embodiments, receiving an input may include the computing system receiving an input from one or more modules such as, for example, a data processing module that reads one or more meta data tags comprising a lesion type and an anatomical location.

The method of FIG. 7 can also include an act 426 of segmenting the one or more target lesions into regions of interest. Act 426 can comprise analyzing at least one of the one or more target lesions with an image processing module, wherein for the at least one of the one or more target lesions, the image processing module is configured to restrict the total range of pixel intensities to a first restricted range of pixel intensities. Though segmenting the one or more target lesions into regions of interest may comprise restricting the total range of pixel intensities within the one or more target lesions to a restricted range—the region of interest—that does not mean that it is the only way of segmenting the one or more target lesions into regions of interest or that subsets of pixel intensities are the only regions of interest. For example, the computing device 100 may segment the one or more target lesions into regions of interest using an image processing module 110 where the regions of interest may be new metastases or non-target regions of interest.

The method of FIG. 7 can also include an act 428 of extracting a vascular tumor burden and one or more tumor metrics from the regions of interest. Act 428 can comprise analyzing at least one of the one or more target lesions with an image processing module, wherein for the at least one of the one or more target lesions, the image processing module is configured to: identify a total range of pixel intensities; restrict the total range of pixel intensities to a first restricted range of pixel intensities, wherein the first restricted range of pixel intensities corresponds to a first subset of pixel intensities representative of vascularized tumor; and determine one or more lesion metrics. Act 428 may further comprise deriving a vascular tumor burden for the at least one of the one or more target lesions. For example, image processing module 114 may perform the foregoing as described above.

The method of FIG. 7 can also include an act 430 of calculating one or more changes in the vascular tumor burden and the one or more tumor metrics. For example, data processing module 114 or hardware processors 108 of computing system 100 may calculate changes in VTB and one or more tumor metrics. The changes referenced may be changes observed over time with respect to the same lesion.

The method of FIG. 7 can also include an act 432 of deriving an objective tumor response. Act 432 can comprise determining the objective tumor response for the at least one of the one or more target lesions. Act 432 may additionally comprise, but in some embodiments may not further comprise, wherein the objective tumor response is based on the vascular tumor burden. For example, the objective tumor response may be derived from any of one or more tumor response criteria and the requisite one or more lesion metrics. Computing system 100 may automatically analyze each of the one or more lesions in light of the one or more tumor response criteria, collecting the requisite lesion metrics to calculate the corresponding objective tumor response. Additionally or alternatively, the objective tumor response may be based, at least in part, on the VTB as defined above.

The method of FIG. 7 can also include an act 434 of generating and displaying a detailed summary display comprising the objective tumor response and the one or more lesion metrics. Act 434 can comprise displaying a customizable summary image, wherein the customizable summary image comprises: a first illustration, wherein the first illustration comprises an illustration of the at least one of the one or more target lesions at the first point in time; a second illustration, wherein the second illustration comprises an illustration of the at least one of the one or more target lesions at the second point in time; and at least one additional component. For example, the detailed summary display (i.e., the detailed summary image) may be displayed at computing system 100 through I/O device interface 106 or may be transferred through network 128 to computing device 120, where a user may view the detailed summary image from a display associated with the computing device 120.

Figure 8:
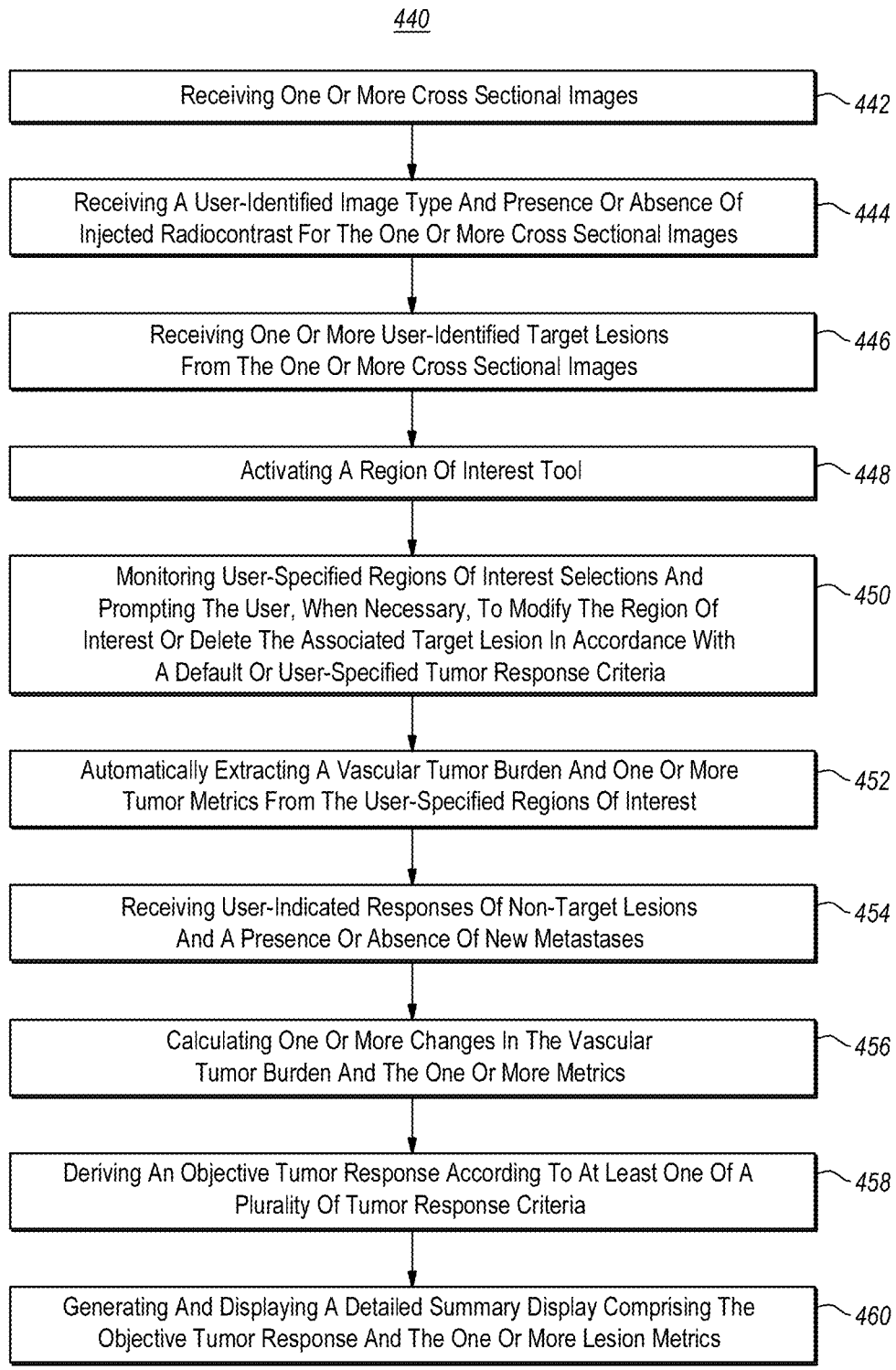
FIG. 8 illustrates a computer-implemented method of determining an objective tumor response to an anti-cancer therapy through user-interaction with a computer interface provided in accordance with one or more embodiments of the present disclosure.

Referring now to FIG. 8, FIG. 8 shows that the method 440 for generating and displaying a detailed summary display can include an act 442 of receiving one or more cross-sectional images. Act 442 comprises receiving one or more cross-sectional images, wherein the one or more cross-sectional images comprise one or more cross-sectional slices of digital medical image data from a radiologic device. For example, computing system 100 may receive one or more cross-sectional images 102 from radiologic device 104, or in some embodiments, computing system 100 may receive one or more cross-sectional images from storage database system 124. Additionally or alternatively, computing system 100 may receive one or more cross-sectional images from a combination of radiologic device 104 and storage database system 124.

The method of FIG. 8 can also include an act 444 of receiving a user-identified image type and presence or absence of injected radiocontrast for the one or more cross-sectional images. Act 444 can comprise receiving one or more inputs, wherein the one or more inputs comprise a determination of injected radiocontrast in any of the one or more cross-sectional images. For example, computing system 100 may receive user-identified image type and a presence or absence of injected radiocontrast through I/O device interface 106 such that a user selects the foregoing using computing device 120, which may access the I/O device interface 106 of computing system 100 through network 126. Additionally or alternatively, user-identified image type and presence or absence of injected radiocontrast may be received directly at computing system 100 by the user.

The method of FIG. 8 can also include an act 446 of receiving one or more user-identified target lesions from the one or more cross-sectional images. Act 446 can comprise identifying one or more target lesions within the one or more cross-sectional images. For example, a user, through computing device 120 or directly at computing system 100 may identify target lesions from the one or more cross-sectional images using I/O device interface 106.

The method of FIG. 8 can also include an act 448 of activating a region of interest tool. For example, I/O device interface 106 may comprise a region of interest tool that allows a user to select one or more regions of interest. As an additional example, the activated region of interest tool may be a slider-based scale wherein the user may be able to select a range of pixel intensities.

The method of FIG. 8 can also include an act 450 of monitoring user-specified regions of interest selections and prompting the user, when necessary, to modify the region of interest or delete the associated target lesion in accordance with a default or user-specified tumor response criteria. For example, one or more tumor response criteria may be pre-defined at computing system 100 or may be selectable by a user through I/O device interface 106. Each of the one or more tumor response criteria comprises particular rules and guidelines. Computing system 100 may be programmed to only accept target lesions—or other regions of interest—that conform to the rules and guidelines of the one or more tumor response criteria that are in force within computing system 100. In some embodiments, computing system 100 may prompt the user to modify the region of interest or delete the associated target lesion if it does not qualify as a region of interest according to whatever one or more tumor response criteria are being used and the prompt may be sent to the user through I/O device interface 106.

The method of FIG. 8 can also include an act 452 of automatically extracting a vascular tumor burden and one or more tumor metrics from the user-specified regions of interest. Act 452 can comprise analyzing at least one of the one or more target lesions with an image processing module, wherein for the at least one of the one or more target lesions, the image processing module is configured to: identify a total range of pixel intensities; restrict the total range of pixel intensities to a first restricted range of pixel intensities, wherein the first restricted range of pixel intensities corresponds to a first subset of pixel intensities representative of vascularized tumor; and determine one or more lesion metrics, and act 452 may further comprise deriving a vascular tumor burden for the at least one of the one or more target lesions. The VTB may be extracted or derived as described within this disclosure. In some embodiments, an image processing module 110 automatically extracts the one or more tumor metrics automatically.

The method of FIG. 8 can also include an act 454 of receiving user-indicated responses of non-target lesions and a presence or absence of new metastases. Act 454 can comprise receiving one or more inputs, wherein the one or more inputs comprise a determination of injected radiocontrast in any of the one or more cross-sectional images, data related to a response of one or more non-target lesions, and a presence of one or more new metastases. For example, the user-indicated responses and/or user inputs may be received at computing system 100 through I/O device interface 106.

The method of FIG. 8 can also include an act 456 of calculating one or more changes in the vascular tumor burden and the one or more metrics. For example, the VTB and metrics associated with two temporally spaced lesions may be compared by data processing module 114 from which it may calculate one or more changes.

The method of FIG. 8 can also include an act 458 of deriving an objective tumor response according to at least one of a plurality of tumor response criteria. Act 458 can comprise determining the objective tumor response for the at least one of the one or more target lesions. Act 458 may additionally comprise, but in some embodiments may not further comprise, wherein the objective tumor response is based on the vascular tumor burden. For example, the objective tumor response may be derived from any of one or more tumor response criteria and the requisite one or more lesion metrics. Computing system 100 may automatically analyze each of the one or more lesions in light of the one or more tumor response criteria, collecting the requisite lesion metrics to calculate the corresponding objective tumor response. Additionally or alternatively, the objective tumor response may be based, at least in part, on the VTB as defined above.

The method of FIG. 8 can also include an act 460 of generating and displaying a detailed summary display comprising the objective tumor response and the one or more lesion metrics. Act 460 can comprise displaying a customizable summary image, wherein the customizable summary image comprises: a first illustration, wherein the first illustration comprises an illustration of the at least one of the one or more target lesions at the first point in time; a second illustration, wherein the second illustration comprises an illustration of the at least one of the one or more target lesions at the second point in time; and at least one additional component. For example, the detailed summary display (i.e., the detailed summary image) may be displayed at computing system 100 through I/O device interface 106 or may be transferred through network 128 to computing device 120, where a user may view the detailed summary image from a display associated with the computing device 120.

Figure 9:
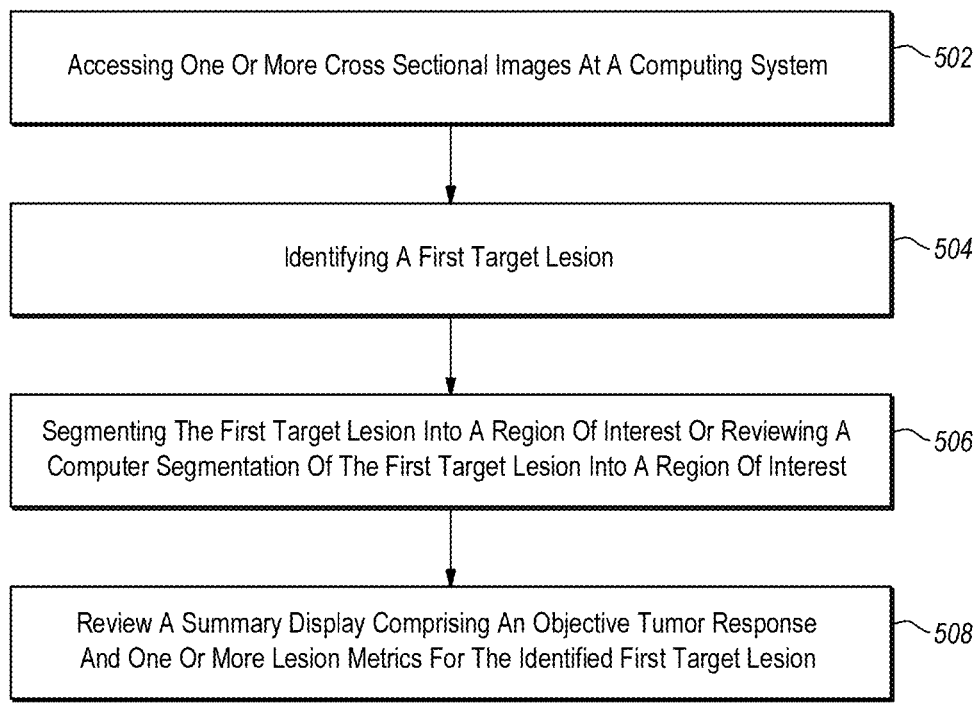
FIG. 9 illustrates a user-implemented method of interacting with a computer interface to determine an objective tumor response to an anti-cancer therapy according to one or more embodiments of the present disclosure.

Referring now to FIG. 9, FIG. 9 shows that the method 500 for reviewing a summary display can include an act 502 of accessing one or more cross-sectional images at a computing system. For example, a user may access one or more cross-sectional images, which may comprise digital medical image data, at computing system 100 through I/O device interface 106. The user may access interface 106 directly at computing system 100 or over network 128 at computing device 120.

The method of FIG. 9 can also include an act 504 of identifying a first target lesion. Act 504 can comprise identifying one or more target lesions within the one or more cross-sectional images. For example, the user may, through interactions with I/O device interface 106, identify a first (or one or more) target lesions using any communications device for transmitting the user-identification to computing system 100, some examples of which include a mouse, keyboard, touchscreen, or other means of identifying and/or selecting information on a user interface that are known in the art.

The method of FIG. 9 can also include an act 506 of segmenting the first target lesion into a region of interest or reviewing a computer segmentation of the first target lesion into a region of interest. For example, the user may segment the first target lesion through interactions with interface 106 either directly at computing system 100 or through network 128 on computing device 120. The user may segment the first target lesion by using a segmenting tool provided at interface 106 or by any other means of segmenting or selecting features of objects or objects, themselves within a digital image, including within digital medical image data. The user may additionally or alternatively review a computer segmentation of the first target lesion using interface 106 and may, in some embodiments, adjust the computer-derived segmentation.

The method of FIG. 9 can also include an act 508 of reviewing a summary display comprising an objective tumor response and one or more lesion metrics for the identified first target lesion. For example, the user may, directly or indirectly review a summary display at the computing system 100 using interface 106. Example outputs of such a review summary are provided in FIGS. 2-5.

Figure 10:
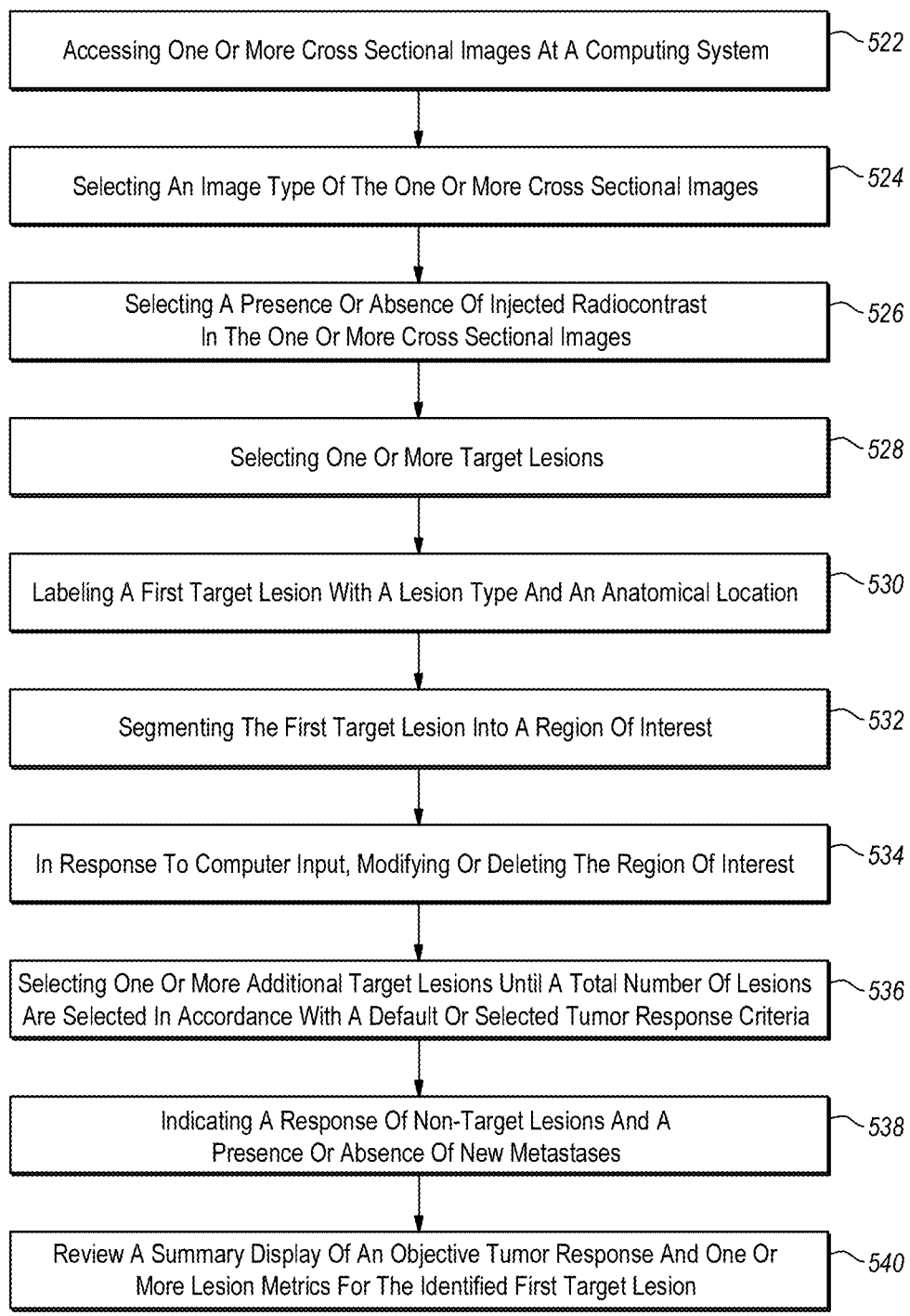
FIG. 10 illustrates a user-implemented method of interacting with a computer interface to determine an objective tumor response to an anti-cancer therapy according to one or more embodiments of the present disclosure.

With reference to FIG. 10, FIG. 10 shows that the method 520 for reviewing a summary display. The method 520 includes method acts 522, 524, 526, 528, 530, 532, 534, 536, 538, and 540. Each of the foregoing methods are performed by a user who may be performing each method act by interacting directly or indirectly with a computing system for determining an objective tumor response to an anti-cancer therapy using one or more cross-sectional images, an example embodiment of which is depicted in FIG. 1. The user interaction with the computing system is performed by interacting with a user interface that the computing system may respond to and which may cause dynamic changes to the resulting summary display and/or to the one or more processes performed by the computing system in determining an objective tumor response. For example, a user may elect which of the one or more tumor response criteria for the computing system to use in determining an objective tumor response. As a further example, the user may select a first or second (or a plurality) of restricted ranges of pixel intensities, which the computer may use in determining the VTB for one or more target lesions.

In some embodiments of FIG. 10, the user, after reviewing the summary display, may perform any or all of the method acts disclosed by FIG. 10 or the user may perform other acts disclosed herein but not explicitly disclosed in FIG. 10. These acts may cause the summary display to dynamically change and/or adjust to the user acts. One benefit of this dynamic interaction is that the user, who in some embodiments is a physician or other healthcare provider, may quickly assess a patient's response to anti-cancer therapy, including AAG therapy, and make adjustments to the patient's treatment regimen as necessary and based on the data. This is particularly beneficial due to the high error rate using traditional methods for determining an objective tumor response based on any of the one or more tumor response criteria. This provides additional technical benefits in that longitudinal comparisons throughout the patient's treatment history may be made or referenced quickly and accurately, and the results may further be used in large (or small) scale statistical analyses for predicting the efficacy of various therapies to one or more tumor types and/or tumor anatomical locations.

Referring now to the method of FIG. 10, it can include an act 522 of accessing one or more cross-sectional images at a computing system. For example, a user may access one or more cross-sectional images, which may comprise digital medical image data, and may do so as described above.

The method of FIG. 10 can also include an act 524 of selecting an image type of the one or more cross-sectional images. For example, the user may select the image type from a drop down menu, a clickable menu, by entering the type manually, or by any other means known in the art for selecting an option from a finite list or manually inputting data. Non-limiting examples of the image types include a CT image, an MRI image, a PET image, a SPECT image, and a CTP image.

The method of FIG. 10 can also include an act 526 of selecting a presence or absence of injected radiocontrast in the one or more cross-sectional images. For example, a user may select one of the binary options of injected radiocontrast for the one or more cross-sectional images. This act 526 may be performed by selecting a box answering a question as to whether the one or more images contain injected radiocontrast, maybe a clickable selection, selected from a pull-down menu, or by any other means known in the art for selecting an option.

The method of FIG. 10 can also include an act 528 of selecting one or more target lesions. Act 528 can comprise identifying one or more target lesions within the one or more cross-sectional images. For example, the user may, through interactions with an interface as described above, select one or more target lesions using any communications device for transmitting the user-identification to computing system 100, some examples of which include a mouse, keyboard, touchscreen, or other means of identifying and/or selecting information on a user interface that are known in the art. In some embodiments, selecting the one or more target lesions may comprise the user tracing the target lesion, using a smart-selection tool that, upon selecting a portion of the target lesion, selects an area having similar pixel contrast, or other means of selecting as known in the art.

The method of FIG. 10 can also include an act 530 of labeling a first target lesion with a lesion type and an anatomical location. For example, the user may label a first target lesion with a lesion type (e.g., primary tumor, metastasis, or lymph node) by clickably selecting the lesion type, wherein in some embodiments, the clickable selection is located on a side bar of the user interface and comprises a primary tumor, metastasis, or lymph node; selecting the lesion type from a list or pull-down menu, manually entering the lesion type, or other means known in the art for labeling a digital image or digital medical image data. The user may similarly label a first target lesion with an anatomical location. In some embodiments, the anatomical locations are pre-set to encourage consistency of labeling. For example, the user will select one of the pre-set labels, including, for example, "lung" so as to avoid potential user labels for the same anatomical location such as, for example, "lung_targetlesion1," "right lung," "lung1," etc.

The method of FIG. 10 can also include an act 532 of segmenting the first target lesion into a region of interest. Act 532 may be repeated iteratively if there are more than one regions of interest. For example, the user may segment the first target lesion by using a segmenting tool provided at the interface, may manually trace the regions of interest, or may segment the target lesion using any other means of segmenting or selecting features of objects, or objects themselves, within a digital image, including within digital medical image data.

The method of FIG. 10 can also include an act 534 of in response to computer input, modifying or deleting the region of interest. For example, the computing system may be using one or more tumor response criteria which require regions of interest to be a certain size, and if computer may provide input to the user, such as, "the region of interest is too small" wherein the user modifies the region of interest, if possible, to accommodate the computer input. If the region of interest cannot be modified sufficiently by the user or the input is that too many regions of interest have been selected, the user may delete and/or remove the region of interest. In some embodiments, deleting the region of interest acts to remove the user placed selection without having an effect on the underlying digital image.

The method of FIG. 10 can also include an act 536 of selecting one or more additional target lesions until a total number of lesions are selected in accordance with a default or selected tumor response criteria. For example, the user may repeat method acts 528, 530, 532, and 534 until the total number of lesions are selected in accordance with a default or selected tumor response criteria. Additionally or alternatively, the user may be directed to act 536 if the selected tumor response criteria are changed by the user or by the computing system.

The method of FIG. 10 can also include an act 538 of indicating a response of non-target lesions and a presence or absence of new metastases. For example, the user may indicate a response by selecting the non-target response from a pull-down menu, by entering the response manually, or by any other means known in the art for selecting a response. The user may also select the presence or absence of new metastases by clickably selecting "Yes" or "No" in response to the prompt: "New Metastasis," or similar. Additionally or alternatively, the user may select the presence or absence of new metastases by using a pull-down menu, entering the response manually, or by any other means known in the art.

The method of FIG. 10 can also include an act 540 of reviewing a summary display of an objective tumor response and one or more lesion metrics for the identified first target lesion. For example, the user may, directly or indirectly review a summary display, example outputs of such provided in FIGS. 2-5. The user may optionally return to any of the method acts in FIG. 10, make one or more changes, and return to method act 540, wherein the summary display may be updated with the one or more changes.

Example 1

The following Table 1 lists abbreviations/acronyms used in any of Tables 2-4 together with their meaning.

TABLE 1

List of Acronyms/Abbreviations

| Acronym/Abbreviation | Meaning |
|---|---|
| RECIST | Response Evaluation Criteria in Solid Tumors |
| PFS | Progression-Free Survival |
| OS | Overall Survival |
| CI | Confidence Interval |
| PR | Partial Response |

TABLE 1-continued

List of Acronyms/Abbreviations

| Acronym/Abbreviation | Meaning |
|---|---|
| SD | Stable Disease |
| PD | Progressive Disease |
| HR | Hazard Ratio |
| FR | Favorable Response |
| IR | Intermediate Response |
| UR | Unfavorable Response |

Tables 2-4 include experimental and/or clinical data described immediately below and within FIG. 11. Particularly, the disclosed hazard ratio (HR) is the ratio of the hazard rates corresponding to the responder and nonresponder groups. The hazard rates indicate the likelihood of progression-free survival (PFS) of the entire group. The VTB Criteria has a HR of 5.7, indicating that the nonresponders were 5.7 times more likely to progress than the responders. In Table 2, the p-values are calculated with respect to the indicated comparison.

In patients with metastatic clear-cell renal cell carcinoma, VTB Criteria nonresponders (N=120 patients with <30% decrease or an increase in the VTB or new metastases) on the initial post-therapy CT study were 5.7 times more likely to progress (HR=5.70, 95% CI=4.07-7.97, p<0.001) than responders (N=155 patients with >30% decrease in the VTB). The average percent decrease in VTB of 33.8% following one round of AAG therapy in the full patient cohort (N=275) was significantly greater (p<0.001) than the average percent decrease in tumor length of 9.5%. While percent change in length was highly correlated with percent change in area (r=0.939), neither were as strongly correlated with percent change in VTB (r=0.713 and 0.764, respectively), indicating that percent change in VTB is a unique size metric. In a patient level analysis, inter-observer agreement was very good for assessing percent change in length, area, and VTB (ICC=0.82, 0.89, and 0.88, respectively) but poor for assessing percent change in mean attenuation (ICC=0.31), which is used in Choi Criteria and Modified Choi Criteria. These findings indicated that quantitative changes in the VTB using the computer-assisted tumor response assessment as disclosed herein are strongly predictive of patient survival, highly predictive of tumor response to AAG therapy, and highly reproducible.

TABLE 2

Figure 11:
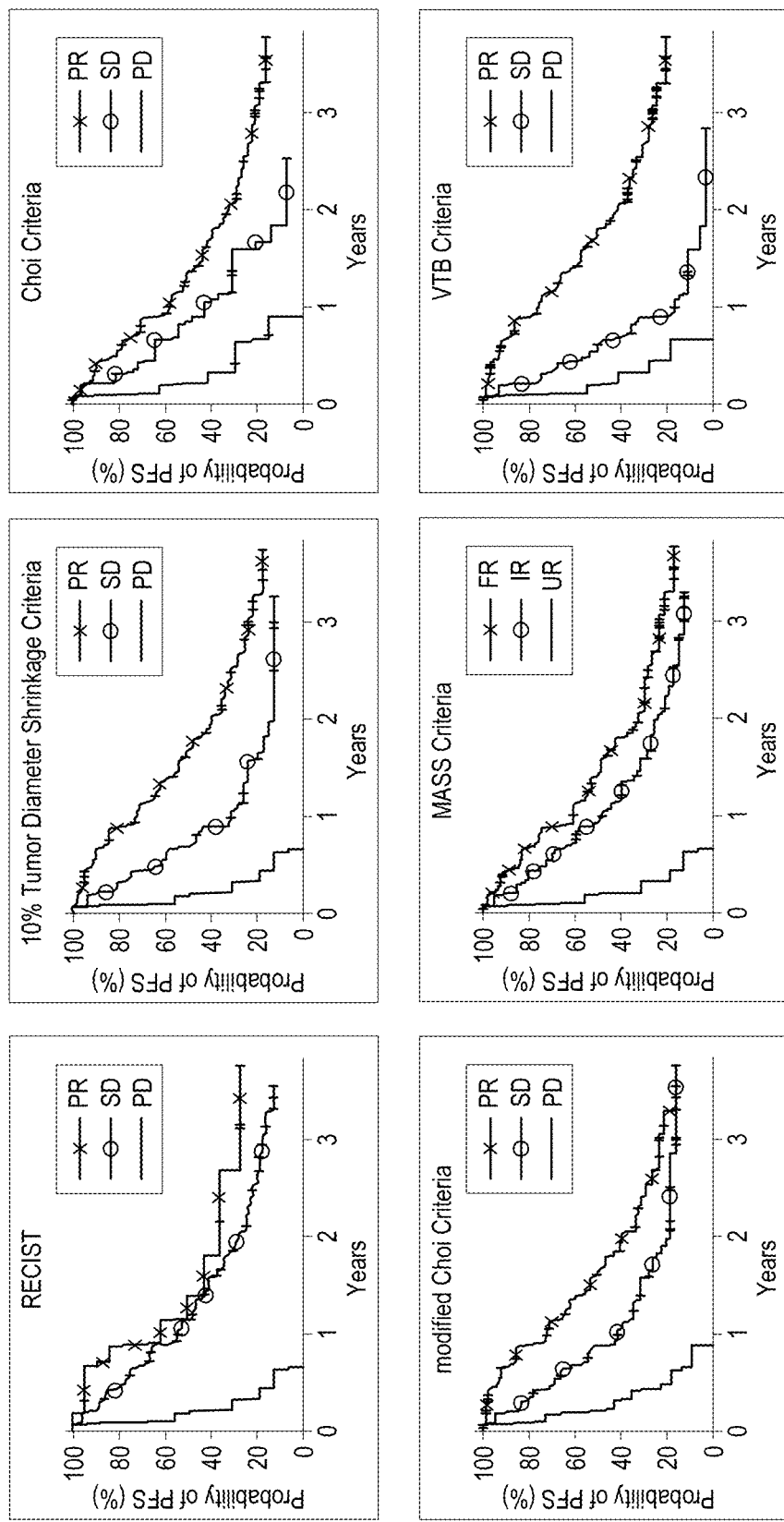
FIG. 11 illustrates the results from a large clinical validation study, expressing how the VTB Criteria better predicts tumor response to anti-angiogenic therapy than other currently used imaging criteria.

Data associated with each sextant of FIG. 11

| | | Sample Size (N) | Median PFS | 95% CI |
|---|---|---|---|---|
| RECIST | PR | 20 | 1.39 | 0.89-∞ |
| | SD | 236 | 1.13 | 0.91-1.40 |
| | PD | 19 | 0.19 | 0.09-0.32 |
| 10% Tumor Shrinkage | PR | 138 | 1.65 | 1.38-1.91 |
| | SD | 118 | 0.68 | 0.54-0.88 |
| | PD | 19 | 0.19 | 0.09-0.32 |
| Choi | PR | 207 | 1.27 | 0.98-1.58 |
| | SD | 45 | 0.85 | 0.43-1.12 |
| | PD | 23 | 0.21 | 0.09-0.63 |
| modified Choi | PR | 118 | 1.65 | 1.36-1.94 |
| | SD | 126 | 0.88 | 0.68-1.05 |
| | PD | 31 | 0.21 | 0.19-0.42 |
| MASS | FR | 135 | 1.24 | 0.92-1.60 |
| | IR | 121 | 1.05 | 0.71-1.38 |
| | UR | 19 | 0.19 | 0.09-0.32 |

TABLE 2-continued

Data associated with each sextant of FIG. 11

| | | Sample Size (N) | Median PFS | 95% CI |
|---|---|---|---|---|
| VTB | PR | 155 | 1.79 | 1.41-1.98 |
| | SD | 101 | 0.54 | 0.44-0.68 |
| | PD | 19 | 0.19 | 0.09-0.33 |

TABLE 3

Additional Data associated with each sextant of FIG. 11

| | HR | Responders (N) | Nonresponders (N) | 95% CI | p-value |
|---|---|---|---|---|---|
| RECIST | 1.54 | 255 | 20 | 0.85-2.77 | 0.148 |
| 10% Tumor Shrinkage | 2.98 | 137 | 13 | 2.19-4.05 | <0.001 |
| Choi | 2.52 | 68 | 207 | 1.79-3.55 | <0.001 |
| modified Choi | 2.32 | 157 | 118 | 0.85-2.77 | <0.001 |
| MASS | 1.76 | 140 | 135 | 1.31-2.37 | <0.001 |
| VTB | 5.70 | 120 | 155 | 4.07-7.97 | <0.001 |

TABLE 4

Hazard ratios between response categories of each imaging criteria

| | | PFS | | | OS | | |
|---|---|---|---|---|---|---|---|
| | | HR | 95% CI | p-value | HR | 95% CI | p-value |
| RECIST | PR vs SD | 0.70 | 0.39-1.27 | 0.241 | 0.27 | 0.11-0.67 | 0.005 |
| | PD vs SD | 10.63 | 6.08-18.57 | <0.001 | 4.22 | 2.53-7.04 | <0.001 |
| 10% Tumor Shrinkage | PR vs SD | 0.38 | 0.27-0.52 | <0.001 | 0.37 | 0.27-0.52 | <0.001 |
| | PD vs SD | 6.89 | 3.91-12.14 | <0.001 | 2.77 | 1.64-4.68 | <0.001 |
| Choi | PR vs SD | 0.53 | 0.35-0.79 | 0.002 | 0.55 | 0.37-0.80 | 0.002 |
| | PD vs SD | 3.94 | 2.14-7.25 | <0.001 | 1.52 | 0.86-2.69 | 0.155 |
| Modified Choi | PR vs SD | 0.51 | 0.37-0.71 | <0.001 | 0.42 | 0.29-0.59 | <0.001 |
| | PD vs SD | 5.47 | 3.36-8.92 | <0.001 | 1.92 | 1.22-3.02 | 0.005 |
| MASS | FR vs IR | 0.66 | 0.48-0.90 | 0.009 | 0.64 | 0.46-0.90 | 0.009 |
| | UR vs IR | 8.84 | 4.97-15.69 | <0.001 | 3.65 | 2.14-6.21 | <0.001 |
| VBT | PR vs SD | 0.19 | 0.13-0.27 | <0.001 | 0.33 | 0.24-0.46 | <0.001 |
| | PD vs SD | 3.77 | 2.07-6.86 | <0.001 | 3.24 | 1.91-5.47 | <0.001 |

Example 2

In a large inter-observer analysis study with 11 different readers from 10 different institutions assessing cross-sectional images from 20 patients with metastatic renal cell carcinoma treated with AAG therapy, mean tumor assessment time with computer-assisted tumor response assessment, as disclosed herein, and measurement of the VTB was 50% faster than a routine image viewer and manual data entry (7 vs. 14 min, p<0.001), and patient-level errors were significantly less common (0% vs. 31%, p<0.001). Using the computer-assisted tumor response assessment as disclosed herein, inter-observer agreement was very good for measuring the VTB vs. good for measuring tumor length (intraclass correlation coefficient=0.96 vs. 0.68, p=0.021). These findings suggest that tumor response assessment using the computer-assisted tumor response assessment disclosed herein and measurement of the vascular tumor burden is significantly faster, associated with a marked reduction in errors, and associated with substantial inter-observer agreement compared to manual methods that comprise the current standard of care.

CONCLUSION

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

Embodiments of the present invention may comprise or utilize a special-purpose or general-purpose computer system that includes computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer readable hardware storage devices. Computer-readable media that carry computer-executable instructions and/or data structures are transmission media. Thus, by way of example, and not limitation, embodiments of the invention can comprise at least two distinctly different kinds of computer-readable media: computer readable hardware storage devices and transmission media.

Computer readable hardware storage devices are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer readable hardware storage devices (or vice versa). For example, computer-executable instructions or data structures received over a network or data link can be buffered in RAM within a network interface module (e.g., a "NIC"), and then eventually transferred to computer system RAM and/or to less volatile computer readable hardware storage devices at a computer system. Thus, it should be understood that computer readable hardware storage devices can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some embodiments, such as a cloud-computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

In addition, as used in the specification and appended claims, directional terms, such as "top," "bottom," "up," "down," "upper," "lower," "proximal," "distal," "horizontal," "vertical," "adjacent," and the like are used herein solely to indicate relative directions and are not otherwise intended to limit the scope of the invention or claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system comprising:
   one or more processors; and
   one or more computer-readable hardware storage devices, wherein the one or more computer-readable hardware storage devices comprise computer-executable instructions that, when executed by at least one of the one or more processors, cause the computer system to perform at least the following:
   access an initial total target lesion length for an initial representation of a target lesion in an initial set of one or more cross-sectional images associated with an initial timepoint;
   receive user data identifying the target lesion from one or more cross-sectional images of digital medical image data, the one or more cross-sectional images being associated with a timepoint that is subsequent to the initial timepoint;
   receive additional user data identifying a target lesion type for the identified target lesion, the target lesion type comprising an indication of one of a mass, a metastasis, or a lymph node;
   activate a segmenting tool for segmenting the target lesion into a region of interest;
   automatically identify lesion metrics for the target lesion based on the region of interest, the lesion metrics including a long axis and a short axis for the target lesion;
   receive user data providing a new metastases indication, the new metastases indication indicating whether one or more new sites of disease are represented within the one or more cross-sectional images that are not represented in the initial set of one or more cross-sectional images;

automatically determine a total target lesion length for the target lesion based on the identified lesion metrics for the target lesion and based on the identified target lesion type for the target lesion, wherein:

the total target lesion length includes the long axis for target lesions identified as a mass or a metastasis; and the total target lesion length includes the short axis for target lesions identified as a lymph node; and generate a summary report enabling a user to determine tumor response, the summary report displaying at least the initial total target lesion length, the total target lesion length, and the new metastasis indication.

2. The computer system as in claim 1, wherein the total target lesion length omits the short axis for target lesions identified as a mass or a metastasis, and wherein the target lesion length omits the long axis for target lesions identified as a lymph node.

3. The computer system as in claim 1, wherein the total target lesion length equals a sum of the long axis for target lesions identified as a mass or a metastasis masses and metastases and the short axis for target lesions identified as lymph nodes.

4. The computer system as in claim 1, wherein the computer-executable instructions further include computer-executable instructions that, when executed by the one or more processors, cause the computer system to receive user data identifying a presence or absence of one or more non-target lesions, wherein the one or more non-target lesions represent one or more measurable or non-measurable findings.

5. The computer system as in claim 4, wherein the computer-executable instructions further include computer-executable instructions that, when executed by the one or more processors, cause the computer system to receive user data indicating an observed response for each non-target lesion identified.

6. The computer system as in claim 1, wherein the summary display comprises an illustration of the target lesion, wherein the illustration includes a representation of the long axis and the short axis for the target lesion.

7. The computer system as in claim 6, wherein the summary display includes an indication of the total target lesion length for the target lesion.

8. The computer system as in claim 6, wherein the summary display includes an indication of an observed response for one or more non-target lesions that were identified as present.

9. The computer system as in claim 6, wherein the summary display includes an indication that each target lesion that was identified as a lymph node is a lymph node to differentiate each target lesion that was identified as a lymph node from each target lesion that was identified as a mass or a metastasis.

10. The computer system as in claim 1, wherein the computer-executable instructions further include computer-executable instructions that, when executed by the one or more processors, cause the computer system to export and archive one or more data received, identified, or determined from claim 1 within a storage database system.

11. A method implemented on a computer system for viewing cross-sectional images of medical image data, the method comprising:

accessing an initial total target lesion length for an initial representation of a target lesion in an initial set of one or more cross-sectional images associated with an initial timepoint;

identifying the target lesion from one or more cross-sectional images of digital medical image data, the one or more cross-sectional images being associated with a timepoint that is subsequent to the initial timepoint;

identifying a target lesion type for the target lesion, the target lesion type comprising an indication of one of a mass, a metastasis, or a lymph node;

the computer system activating a segmenting tool for segmenting the target lesion into a region of interest;

the computer system automatically identifying lesion metrics for the target lesion based on the region of interest, the lesion metrics including a long axis and a short axis for the target lesion;

the computer system obtaining a new metastases indication, the new metastases indication indicating whether one or more new sites of disease are represented within the one or more cross-sectional images that are not represented in the initial set of one or more cross-sectional images;

the computer system automatically determining a total target lesion length for the target lesion based on the identified lesion metrics for the target lesion and based on the identified target lesion type for the target lesion, wherein:

the total target lesion length includes the long axis for target lesions identified as a mass or a metastasis; and the total target lesion length includes the short axis for target lesions identified as a lymph node; and the computer system generating a summary report enabling a user to determine tumor response, the summary report displaying at least the initial total target lesion length, the total target lesion length, and the new metastases indication.

12. The method as in claim 11, wherein the total target lesion length omits the short axis for each target lesion of a plurality of target lesions identified as a mass or a metastasis, and wherein the total target lesion length omits the long axis for each target lesion of the plurality of target lesions identified as a lymph node.

13. The method as in claim 11, wherein the total target lesion length equals a sum of the long axis for target lesions identified as a mass or a metastasis masses and metastases and the short axis for target lesions identified as lymph nodes.

14. The method as in claim 11, wherein the summary report further comprises an illustration of the target lesion, wherein the illustration includes a representation of the long axis and the short axis for the target lesion, and wherein the summary report includes an indication of the total target lesion length for the target lesions.

15. The method as in claim 14, wherein the summary report includes an indication of an observed response for one or more non-target lesions identified as present.

16. The method as in claim 14, wherein the summary report includes an indication that each target lesion that was identified as a lymph node is a lymph node to differentiate each target lesion that was identified as a lymph node from each target lesion that was identified as a mass or a metastasis.

17. One or more computer-readable hardware storage devices, wherein the one or more computer-readable hardware storage devices comprise computer-executable instructions that, when executed by one or more processors, are operable to cause a computer system to perform at least the following:
- access an initial total target lesion length for an initial representation of a target lesion in an initial set of one or more cross-sectional images associated with an initial timepoint;
- receive user data identifying the target lesion from one or more cross-sectional images of digital medical image data, the one or more cross-sectional images being associated with a timepoint that is subsequent to the initial timepoint;
- receive additional user data identifying a target lesion type for the target lesion, wherein the target lesion type for the target lesion comprises an indication of one of a mass, a metastasis, or a lymph node;
- activate a segmenting tool for segmenting the target lesion into a region of interest;
- automatically identify lesion metrics for the target lesion based on the region of interest, wherein the lesion metrics include a long axis and a short axis for the target lesion;
- receive a new metastases indication, the new metastases indication indicating whether one or more new sites of disease are represented within the one or more cross-sectional images that are not represented in the initial set of one or more cross-sectional images;
- automatically determine a total target lesion length for the target lesion based on the identified lesion metrics for the target lesion and based on the identified target lesion type for the target lesion, wherein:
  - the total target lesion length includes the long axis for target lesions identified as a mass or a metastasis; and
  - the total target lesion length includes the short axis for target lesions identified as a lymph node; and
- generate a summary report enabling a user to determine tumor response, the summary report displaying at least the initial total target lesion length, the total target lesion length, and the new metastasis indication.

18. The method as in claim 11, wherein, in response to the new metastases indication indicates that one or more new sites of disease are represented within the one or more cross-sectional images that are not represented in the initial set of one or more cross-sectional images, the summary report further displays image data of the one or more cross-sectional images depicting the one or more new sites of disease.

* * * * *